United States Patent
Wexler et al.

(10) Patent No.: US 9,189,973 B2
(45) Date of Patent: *Nov. 17, 2015

(54) SYSTEMS AND METHODS FOR PROVIDING FEEDBACK BASED ON THE STATE OF AN OBJECT

(71) Applicant: OrCam Technologies Ltd., Jerusalem (IL)

(72) Inventors: Yonatan Wexler, Jerusalem (IL); Amnon Shashua, Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/135,775

(22) Filed: Dec. 20, 2013

(65) Prior Publication Data

US 2014/0267645 A1 Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*H04N 7/18* (2006.01)
*G09B 21/00* (2006.01)
(Continued)

(52) U.S. Cl.
CPC .............. *G09B 21/001* (2013.01); *A61F 9/08* (2013.01); *G06F 3/011* (2013.01); *G06F 3/16* (2013.01);
(Continued)

(58) Field of Classification Search
CPC ....... A61F 9/08; G02C 11/10; G06F 17/2765; G06F 3/011; G06F 3/16; G06K 9/00221; G06K 9/00288; G06K 9/00671; G06K 9/74; G08B 3/10; G08B 6/00; G09B 21/00; G09B 21/001; G09B 21/003; G09B 21/006; G10L 13/043; H04N 5/2251
USPC ........................................................... 348/62
See application file for complete search history.

(56) References Cited

U.S. PATENT DOCUMENTS 5,793,900 A * 8/1998 Nourbakhsh et al. .......... 382/263
5,973,618 A * 10/1999 Ellis .............................. 340/990

(Continued)

FOREIGN PATENT DOCUMENTS

EP 2065871 6/2009
EP 2 490 155 8/2012

OTHER PUBLICATIONS

"An Integrated Portable Vision Assistant Agency for the Visual Impaired People" 2009 IEEE International Conference on Control and Automation Christchurch, New Zealand, Dec. 9-11, 2009.*

(Continued)

*Primary Examiner* — Mohammed Rahaman
(74) *Attorney, Agent, or Firm* — Finnegan, Henderson, Farabow, Garrett & Dunner LLP

(57) ABSTRACT

A device and method are provided for providing feedback based on the state of an object. In one implementation, an apparatus for processing images is provided. The apparatus may include an image sensor configured to capture real time images from an environment of a user and at least one processor device configured to initially process at least one image to determine whether an object is likely to change its state. If a determination is made that the object is unlikely to change its state, the at least one processor device may additionally process the at least one image and provide a first feedback. If a determination is made that the object is likely to change its state, the at least one processor device may continue to capture images of the object and alert the user with a second feedback after a change in the state of the object occurs.

20 Claims, 22 Drawing Sheets

(51) Int. Cl.

| | | |
|---|---|---|
| *A61F 9/08* | (2006.01) | |
| *G06K 9/00* | (2006.01) | |
| *H04N 5/232* | (2006.01) | |
| *G08B 3/10* | (2006.01) | |
| *G08B 6/00* | (2006.01) | |
| *G06F 17/27* | (2006.01) | |
| *G06K 9/74* | (2006.01) | |
| *G10L 13/04* | (2013.01) | |
| *G06F 3/16* | (2006.01) | |
| *G06F 3/01* | (2006.01) | |
| *H04N 5/225* | (2006.01) | |
| *G02C 11/00* | (2006.01) | |

(52) U.S. Cl.
 CPC ........ *G06F 17/2765* (2013.01); *G06K 9/00221* (2013.01); *G06K 9/00288* (2013.01); *G06K 9/00671* (2013.01); *G06K 9/74* (2013.01); *G08B 3/10* (2013.01); *G08B 6/00* (2013.01); *G09B 21/00* (2013.01); *G09B 21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G02C 11/10* (2013.01)

(56) References Cited

U.S. PATENT DOCUMENTS

| | | | |
|---|---|---|---|
| 6,115,482 | A | 9/2000 | Sears et al. |
| 7,230,538 | B2 * | 6/2007 | Lai et al. .................... 340/573.1 |
| 2004/0156530 | A1 * | 8/2004 | Brodsky et al. ............... 382/103 |
| 2005/0208457 | A1 * | 9/2005 | Fink et al. ..................... 434/112 |
| 2006/0006235 | A1 | 1/2006 | Kurzweil |
| 2006/0017810 | A1 | 1/2006 | Kurzweil et al. |
| 2010/0088099 | A1 * | 4/2010 | Kurzweil et al. ............. 704/260 |
| 2010/0165091 | A1 * | 7/2010 | Teranishi et al. ............... 348/77 |
| 2012/0212593 | A1 | 8/2012 | Na'aman et al. |
| 2013/0169536 | A1 | 7/2013 | Wexler et al. |
| 2013/0271584 | A1 | 10/2013 | Wexler et al. |

OTHER PUBLICATIONS

Kim et al. "Real Time Traffic Light Recognition System or Color Vision Deficiencies", Proceedings of the 2007 IEEE International Conference on Mechatronics and Automation Aug. 5-8, 2007.*

U.S. Appl. No. 14/136,438, filed Dec. 20, 2013, entitled "Apparatus, Method, and Computer Readable Medium for Expedited Text Reading Using Staged OCR Technique."
U.S. Appl. No. 14/135,727, filed Dec. 20, 2013, entitled "Systems and Method for Audible Facial Recognition."
U.S. Appl. No. 14/137,033, filed Dec. 20, 2013, entitled "Apparatus and Method for Providing Failed-Attempt Feedback Using a Camera on Glasses."
U.S. Appl. No. 14/137,263, filed Dec. 20, 2013, entitled "Apparatus and Method for Executing System Commands Based on Captured Image Data."
U.S. Appl. No. 14/135,757, filed Dec. 20, 2013, entitled "Systems and Methods for Automatic Control of a Continuous Action."
U.S. Appl. No. 14/137,373, filed Dec. 20, 2013, entitled "Apparatus and Method for Automatic Action Selection Based on Image Context."
U.S. Appl. No. 14/135,762, filed Dec. 20, 2013, entitled "Systems and Methods for Performing a Triggered Action."
U.S. Appl. No. 14/137,328, filed Dec. 20, 2013, entitled "Apparatus and Method for Performing Actions Based on Captured Image Data."
U.S. Appl. No. 14/135,859, filed Dec. 20, 2013, entitled "Apparatus Connectable to Glasses."
U.S. Appl. No. 14/137,446, filed Dec. 20, 2013, entitled "Apparatus and Method for Hierarchial Object Identification Using a Camera on Glasses."
U.S. Appl. No. 14/135,928, filed Dec. 20, 2013, entitled "Systems and Methods for Processing Images."
U.S. Appl. No. 14/137,522, filed Dec. 20, 2013, entitled "Apparatus and Method for Using Background Change to Determine Context."
U.S. Appl. No. 14/136,545, filed Dec. 20, 2013, entitled "Apparatus, Method, and Computer Readable Medium for Recognizing Text on a Curved Surface."
U.S. Appl. No. 14/137,384, filed Dec. 20, 2013, entitled "Systems and Methods for Audibly Presenting Textual Information Included in Image Data."
U.S. Appl. No. 14/136,876, filed Dec. 20, 2013, entitled "Apparatus and Method for Analyzing Images."
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).
International Search Report and Written Opinion in International Application No. PCT/IB2014/001168, Mailing date: Oct. 7, 2014.

\* cited by examiner

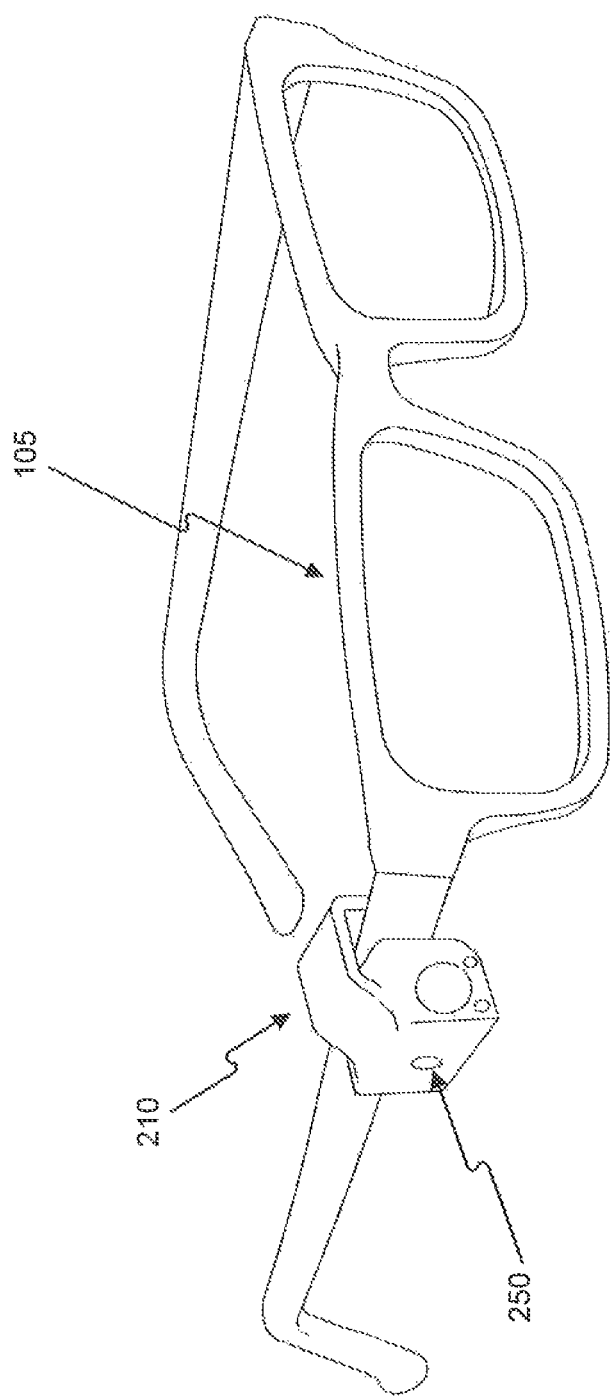

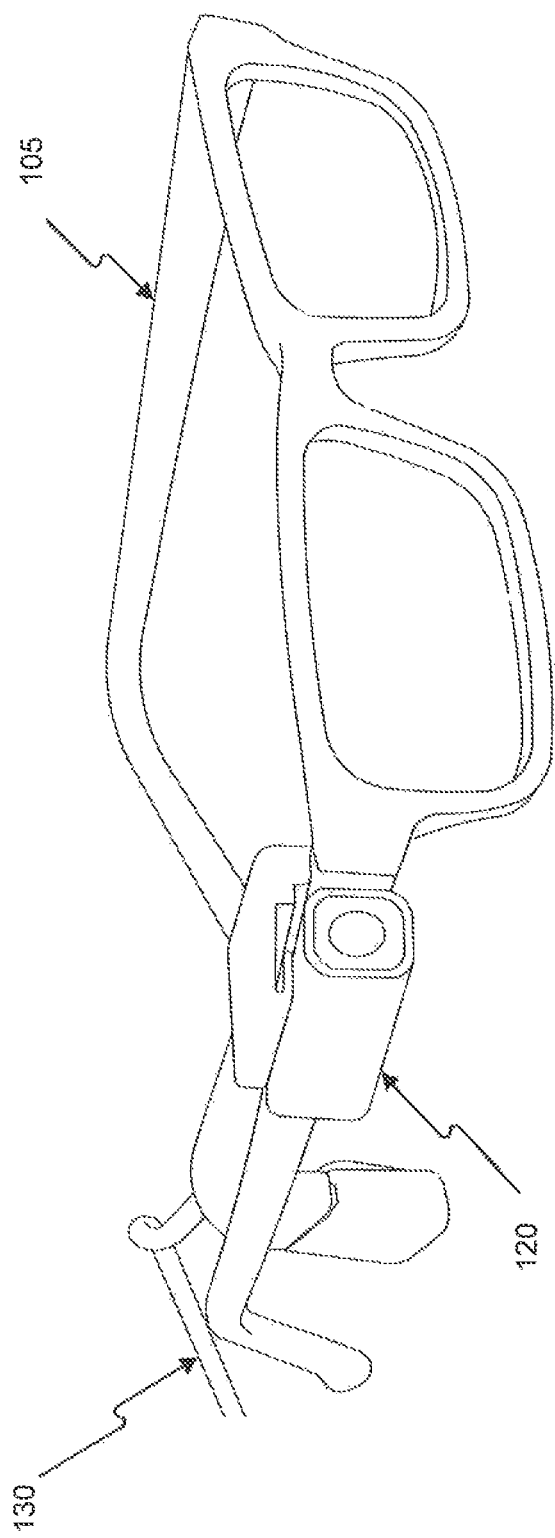

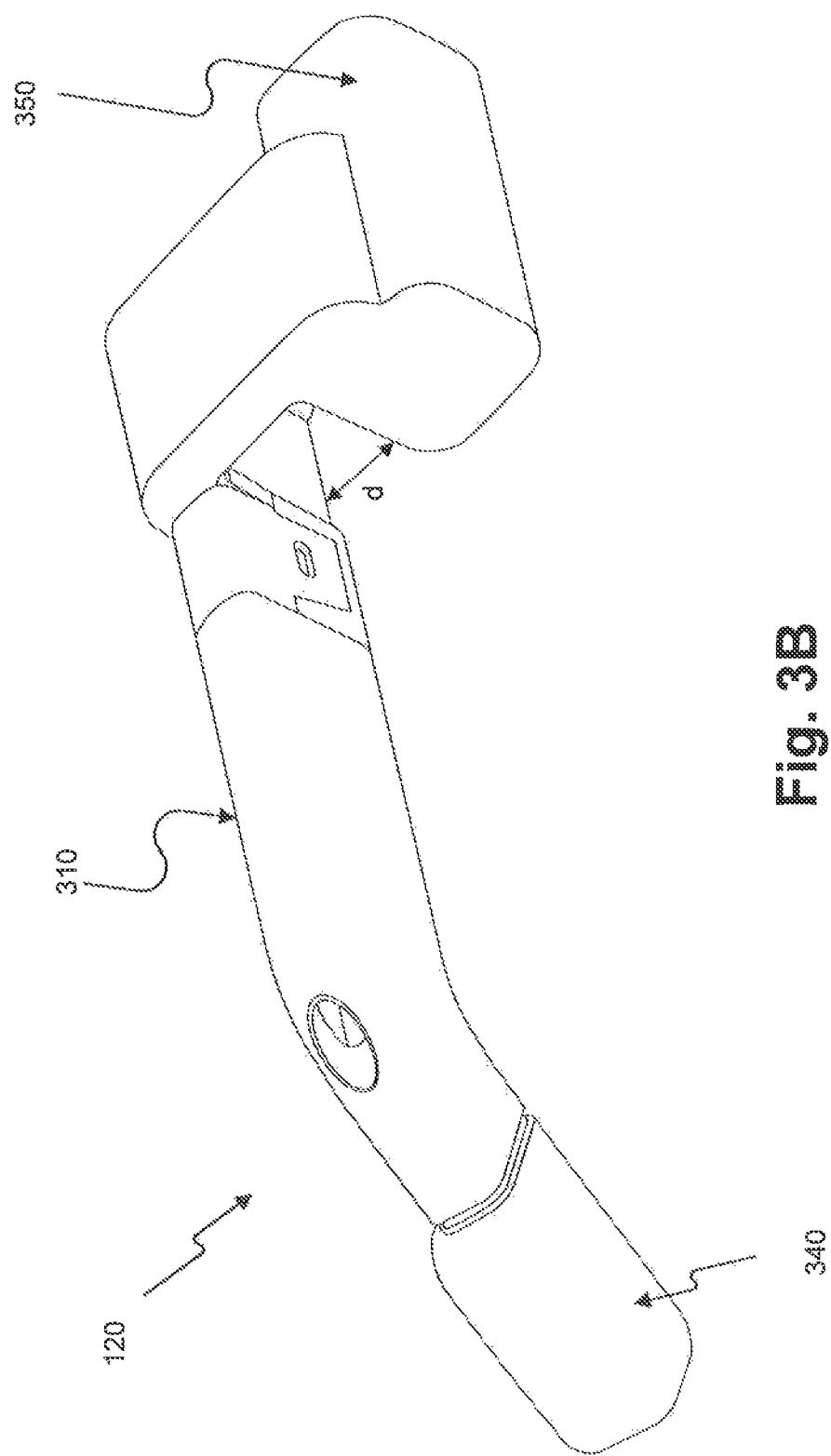

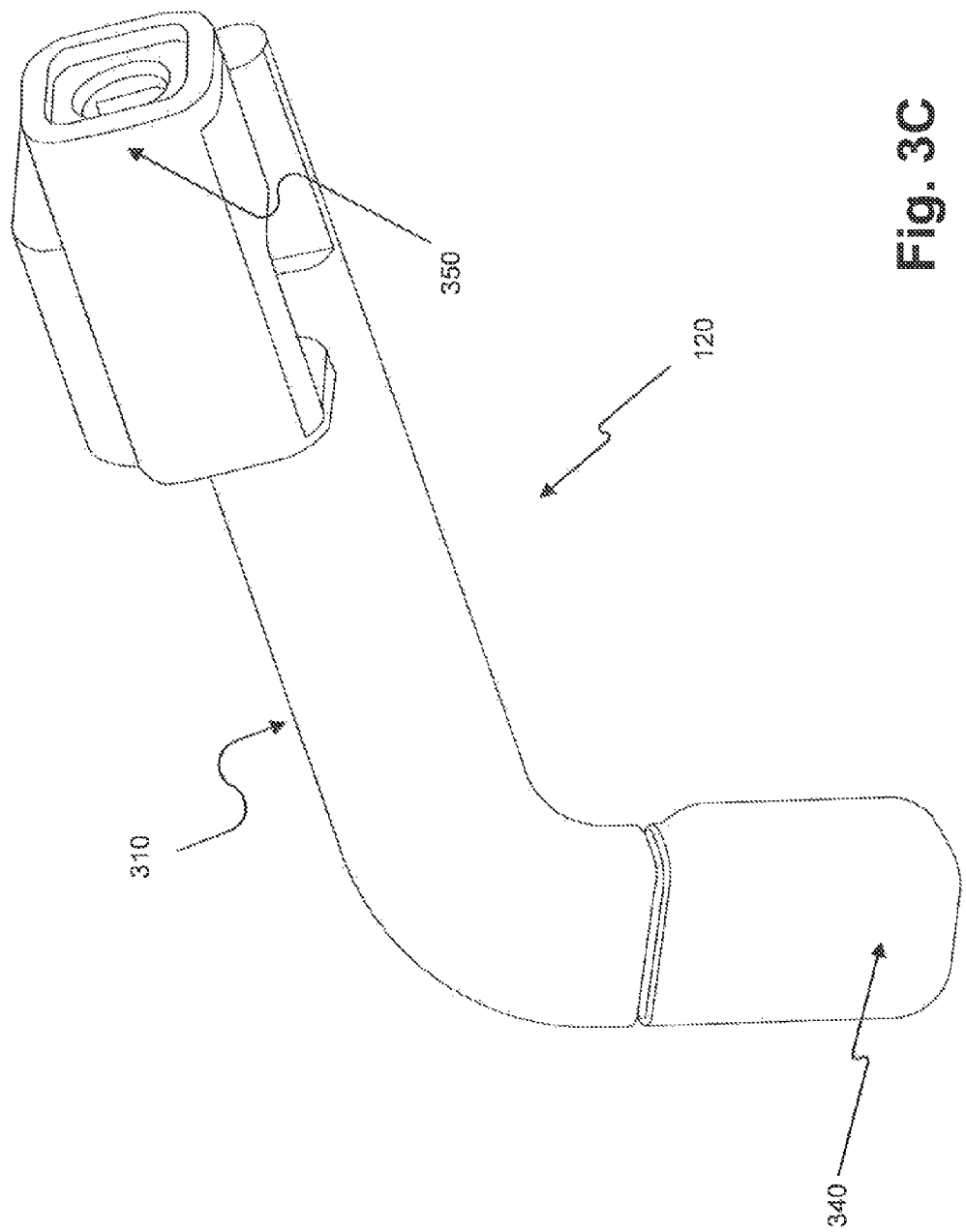

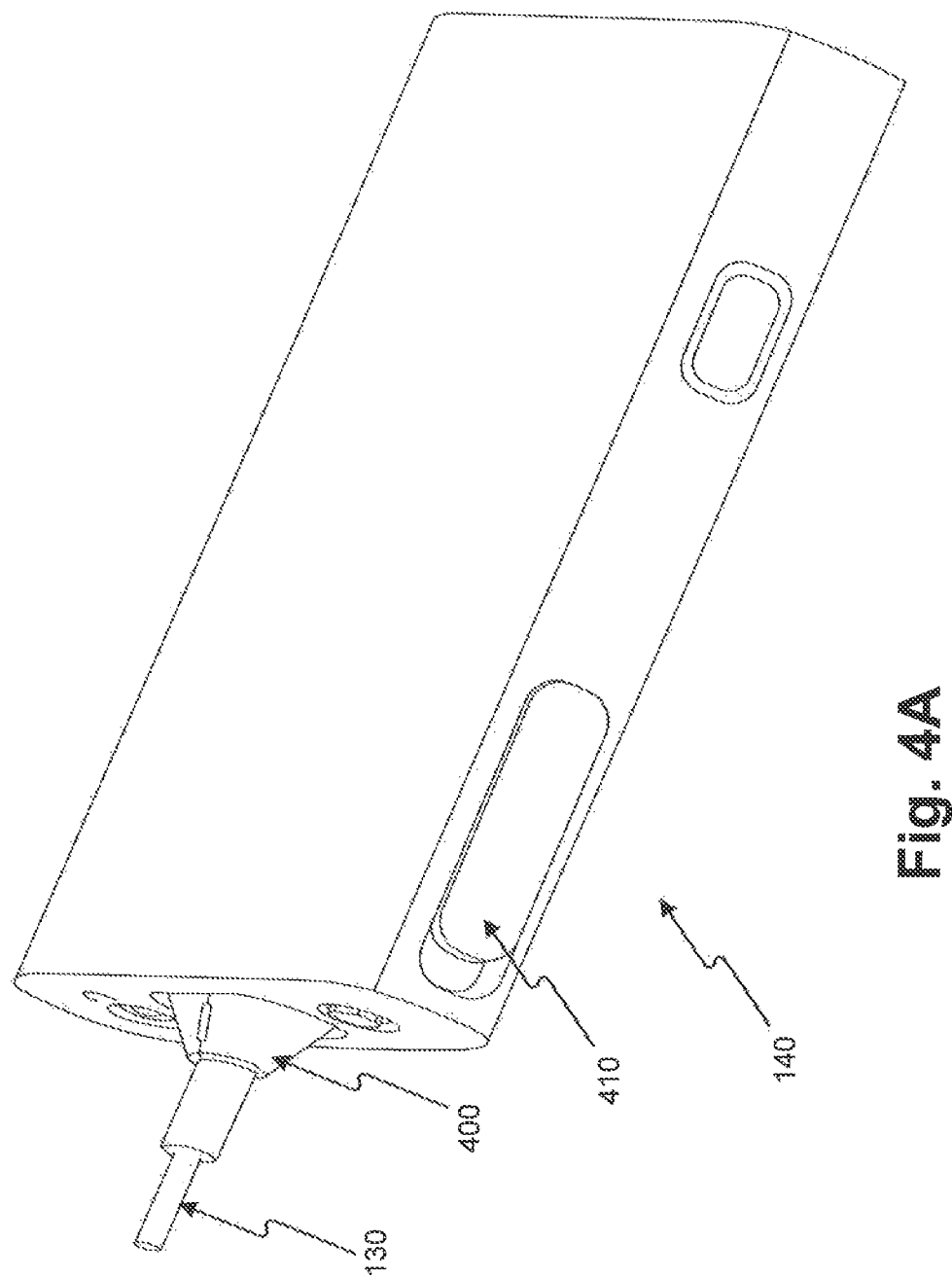

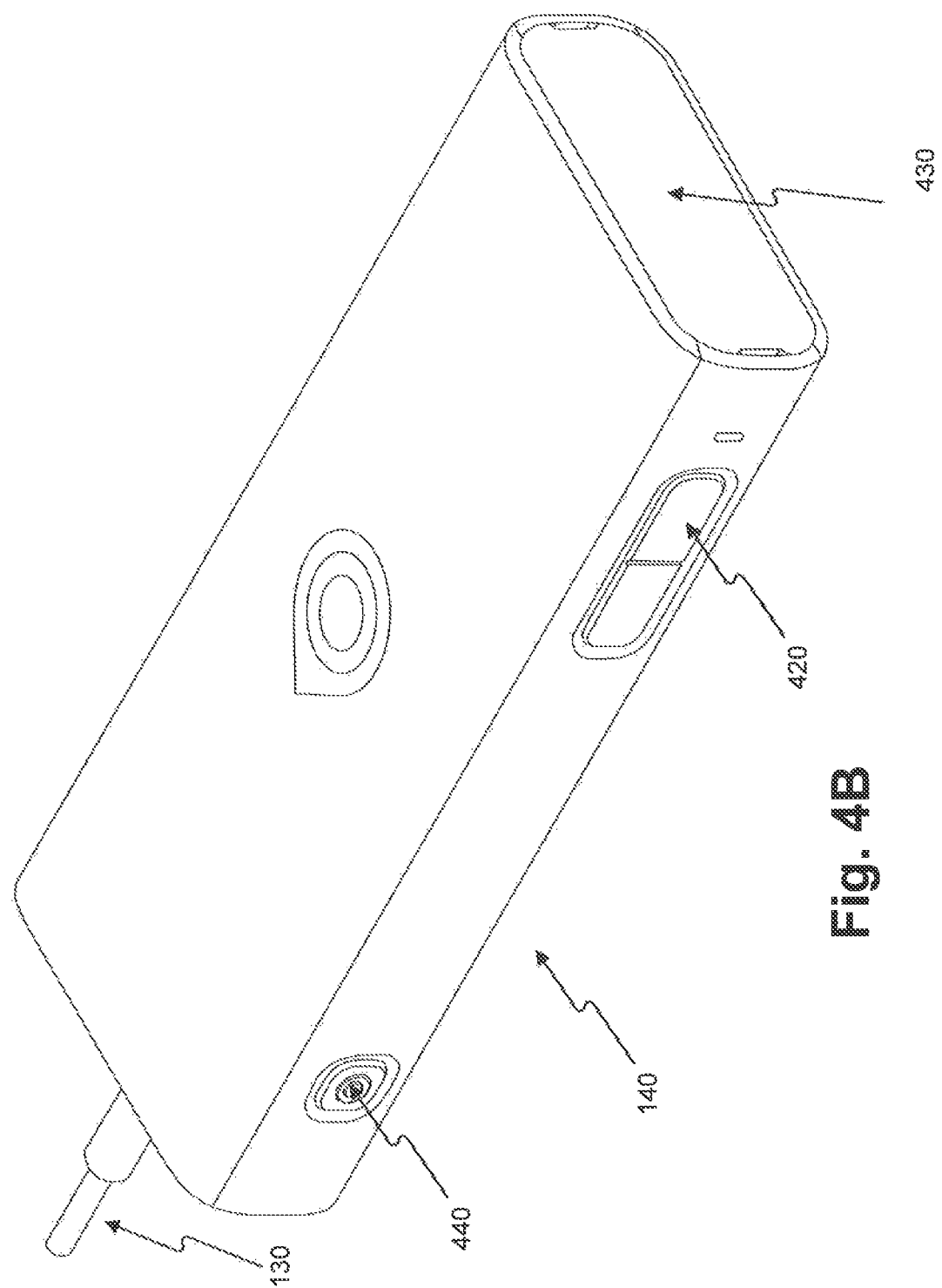

SYSTEMS AND METHODS FOR PROVIDING FEEDBACK BASED ON THE STATE OF AN OBJECT

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus for processing images is disclosed. The apparatus may include an image sensor configured to capture real time images from an environment of a user. The apparatus may also include at least one processor device configured to initially process at least one image to determine whether an object in the environment of the user is likely to change its state. If, during initial processing, a determination is made that the object is unlikely to change its state, the at least one processor device may additionally process the at least one image and provide a first feedback to the user based on the at least one image. If, during initial processing, a determination is made that the object is likely to change its state, the at least one processor device may continue to capture images of the object and alert the user with a second feedback after a change in the state of the object occurs.

In accordance with another disclosed embodiments, an apparatus for processing images is provided. The apparatus may include an image sensor configured to be worn by a user such that a field of view of the image sensor substantially coincides with a field of view of the user, and to capture real time images from an environment of the user. The apparatus may also include at least one processor device configured to process real time images to determine an existence of an object in the field of view of the image sensor and determine whether a state of the object is likely to change. The apparatus may also be configured to track the object while the object remains within the field of view of the image sensor and provide a feedback to the user after the state of the object has changed.

In accordance with another disclosed embodiments, a method for providing feedback to a user is disclosed. The method may include receiving from an image sensor real time image data from an environment of the user, wherein the image sensor is configured to be positioned for movement with a head of the user. The method may also include processing the image data to determine whether a state of an object in the environment of the user is likely to change. The method may further include tracking the object while the object remains within a field of view of the image sensor, if a determination is made that the state of the object is likely to change. The method may additionally include providing an audible feedback to the user after the state of the object has changed.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2C is a schematic illustration of the support shown in FIG. 2A mounted on a pair of glasses;

FIG. 2D is a schematic illustration of a sensory unit attached to the support that is mounted on the pair of glasses shown in FIG. 2C;

FIG. 3B is a schematic illustration of the sensory unit shown in FIG. 3A from a second viewpoint;

FIG. 3C is a schematic illustration of the sensory unit shown in FIG. 3A from a third viewpoint;

FIG. 4A is a schematic illustration of an example of a processing unit from a first viewpoint;

FIG. 4B is a schematic illustration of the processing unit shown in FIG. 4A from a second viewpoint;

DETAILED DESCRIPTION

Figure 1:
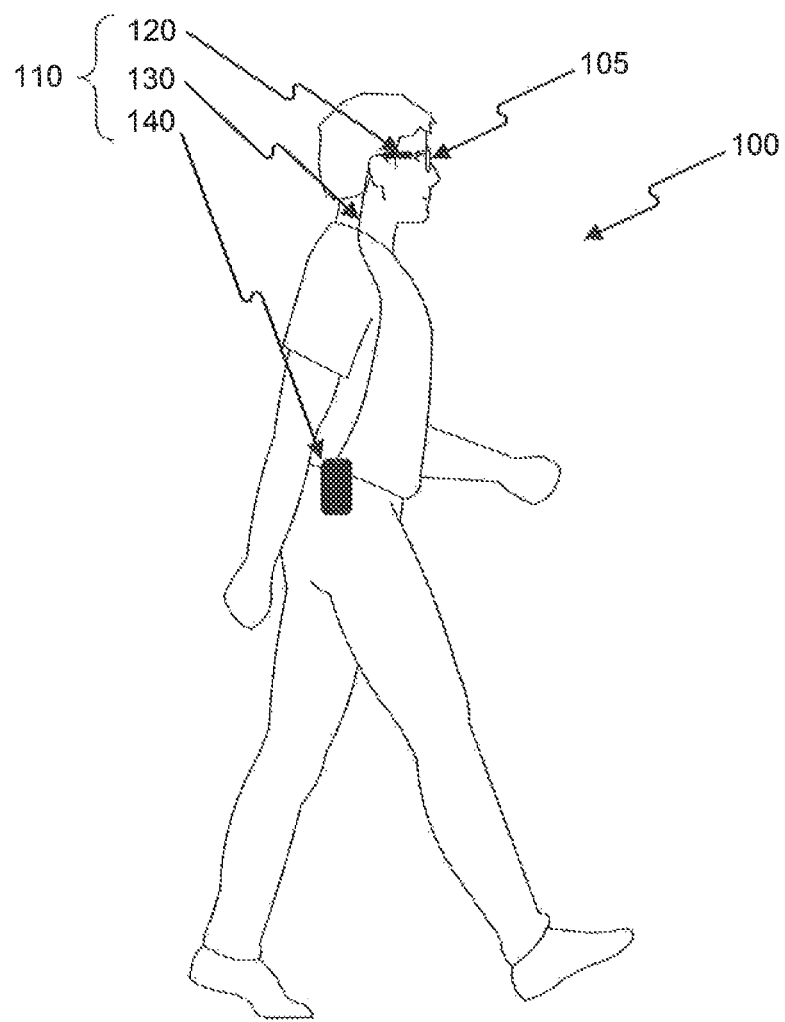
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
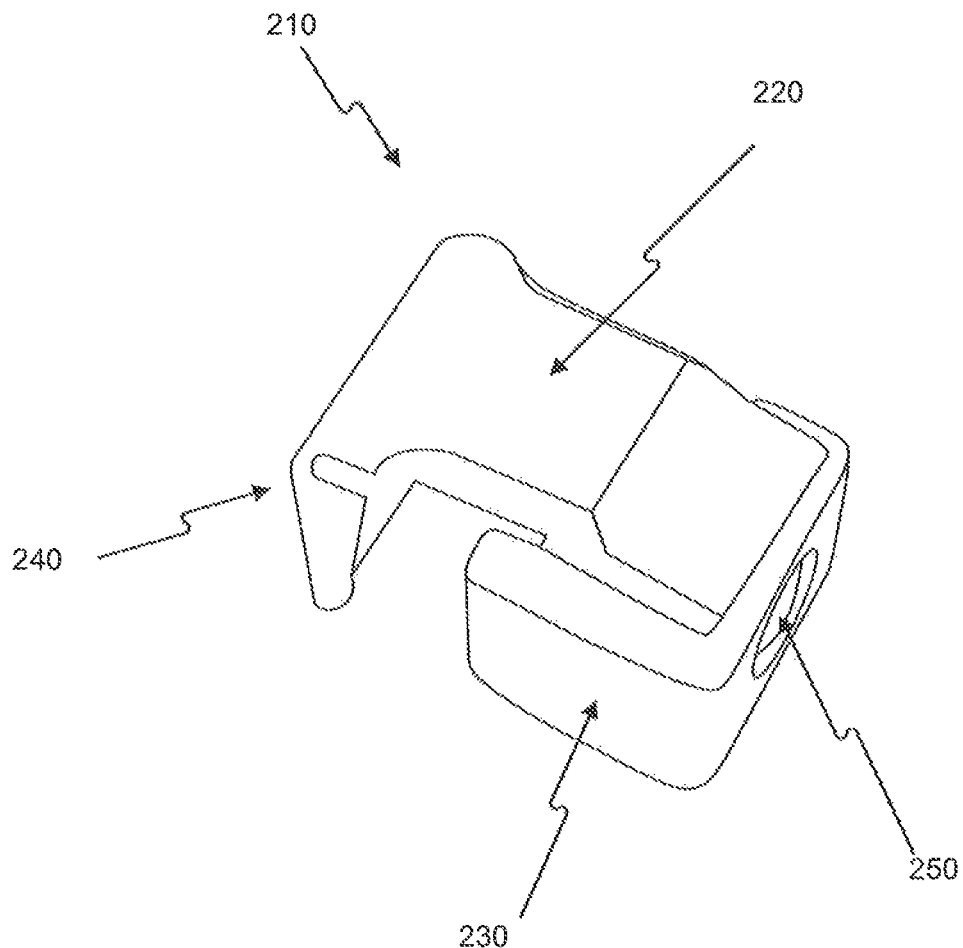
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
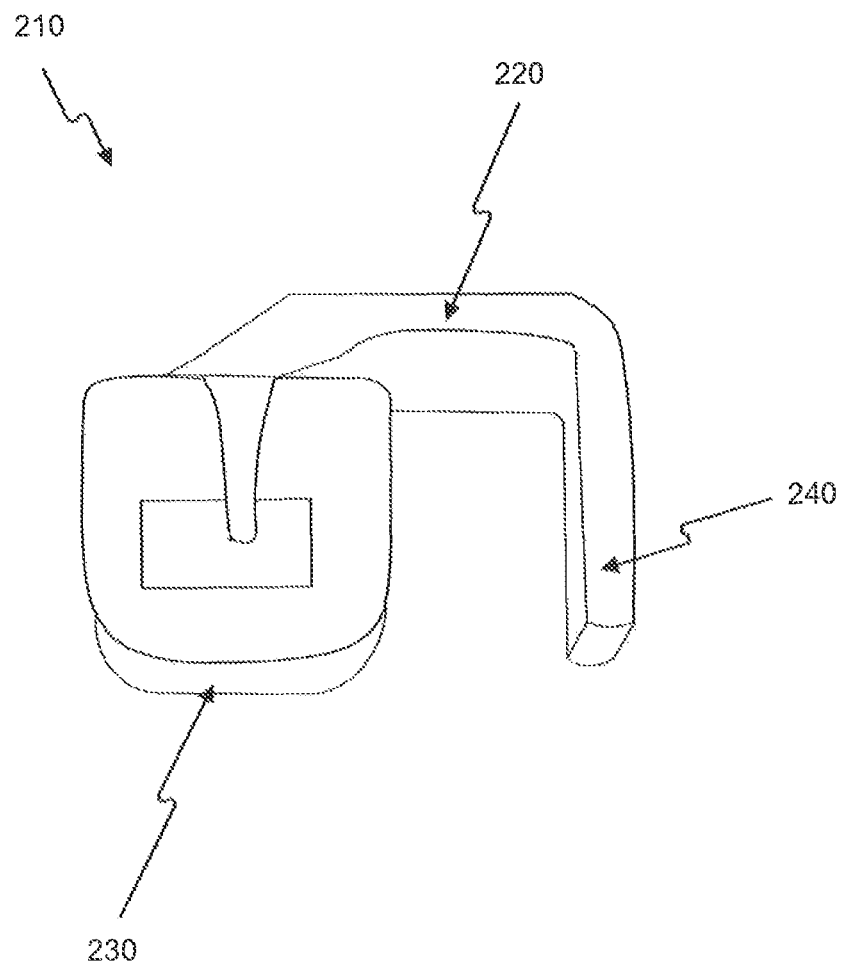
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
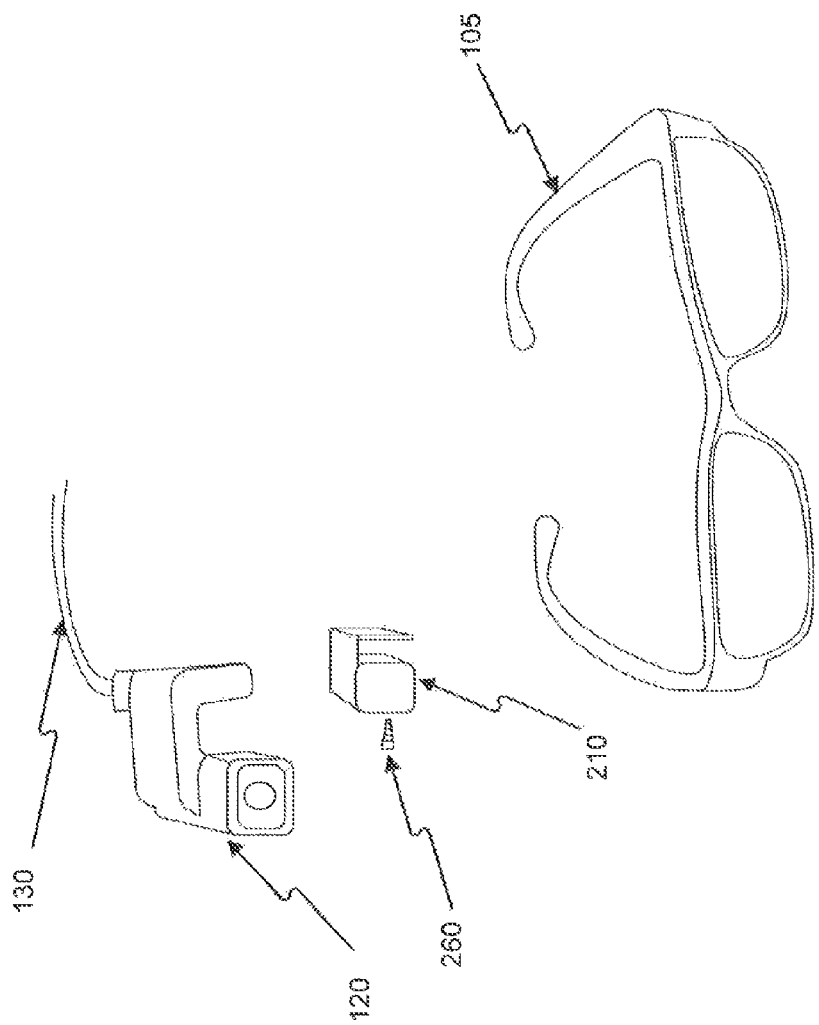
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
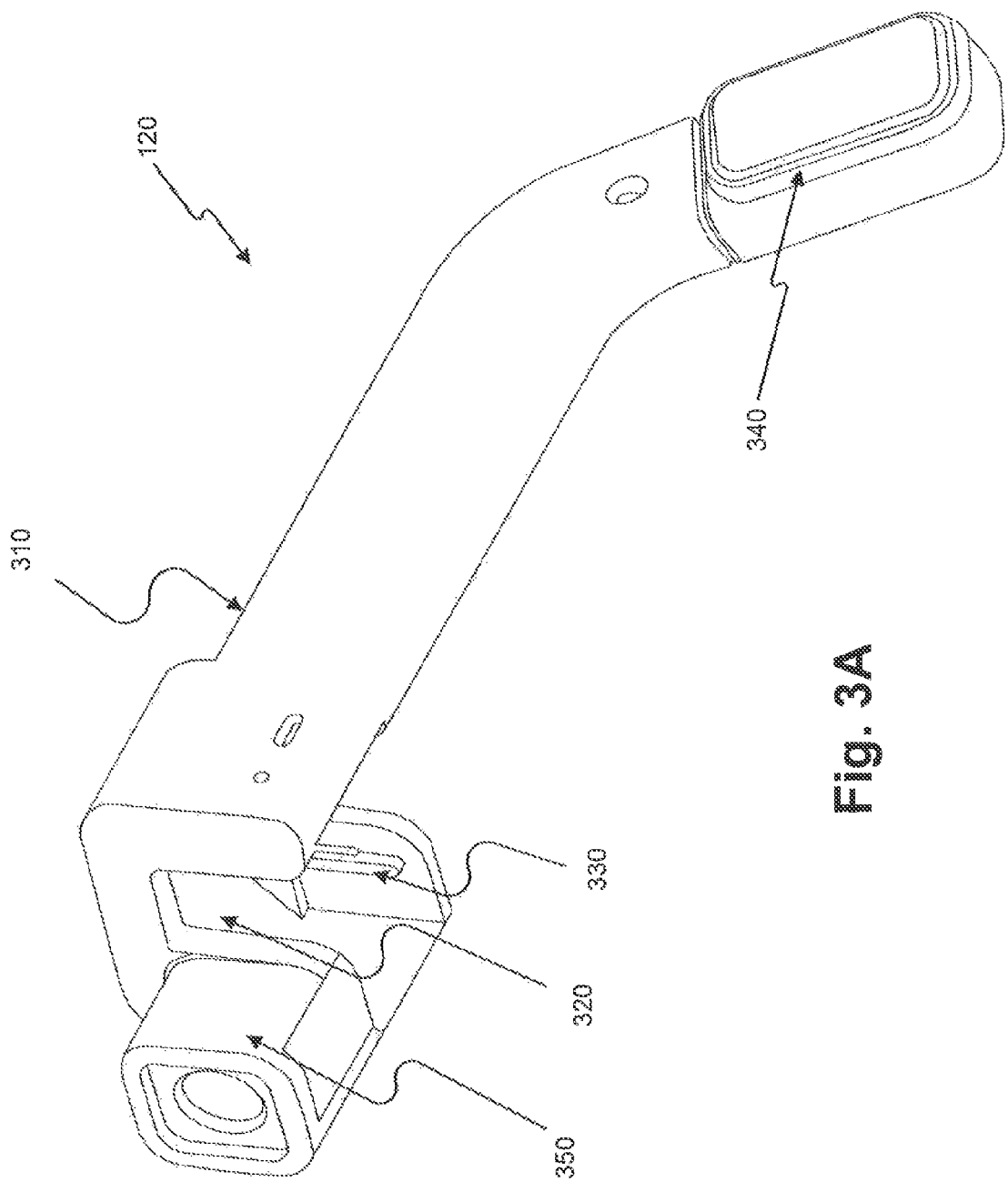
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
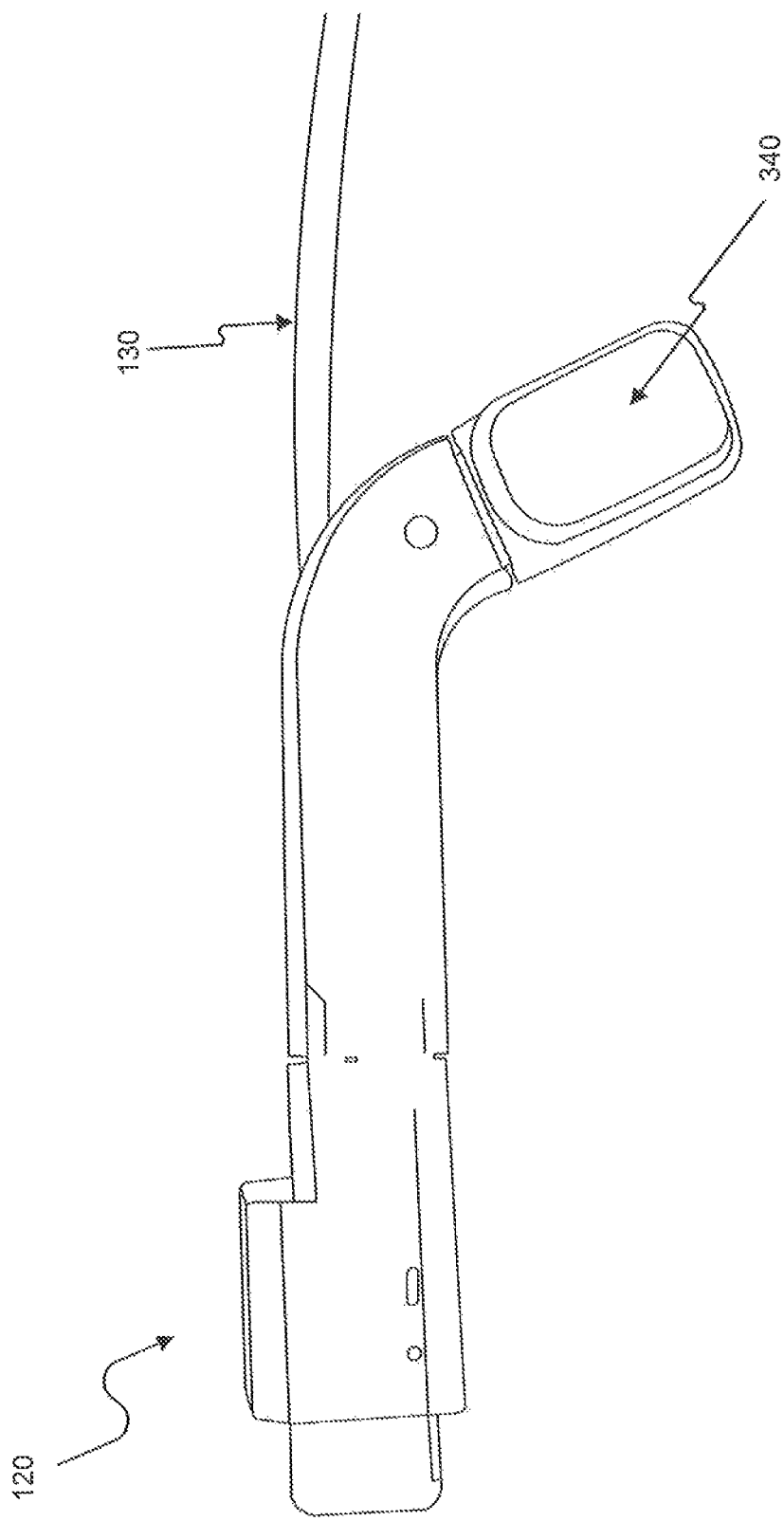
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
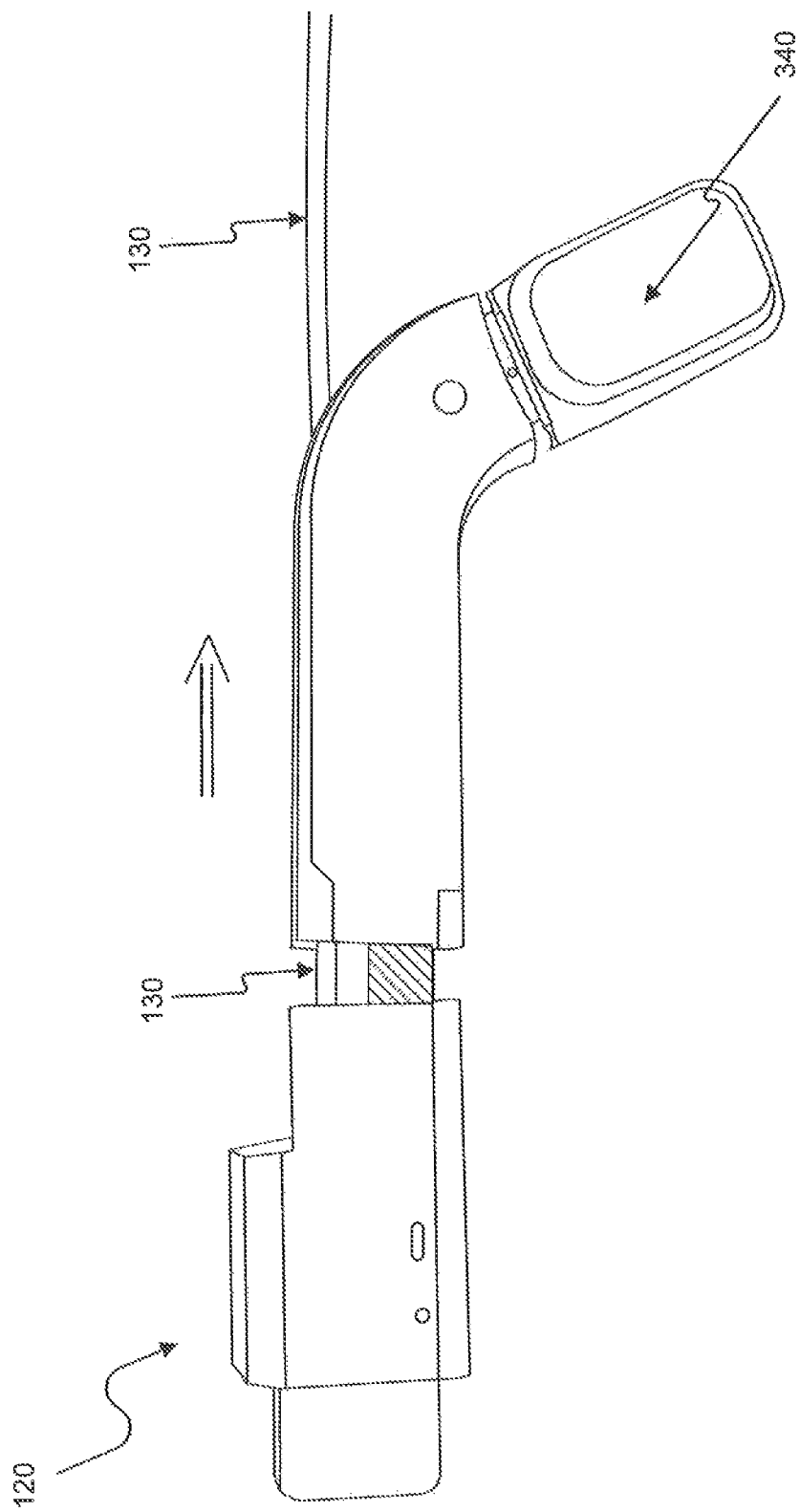
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
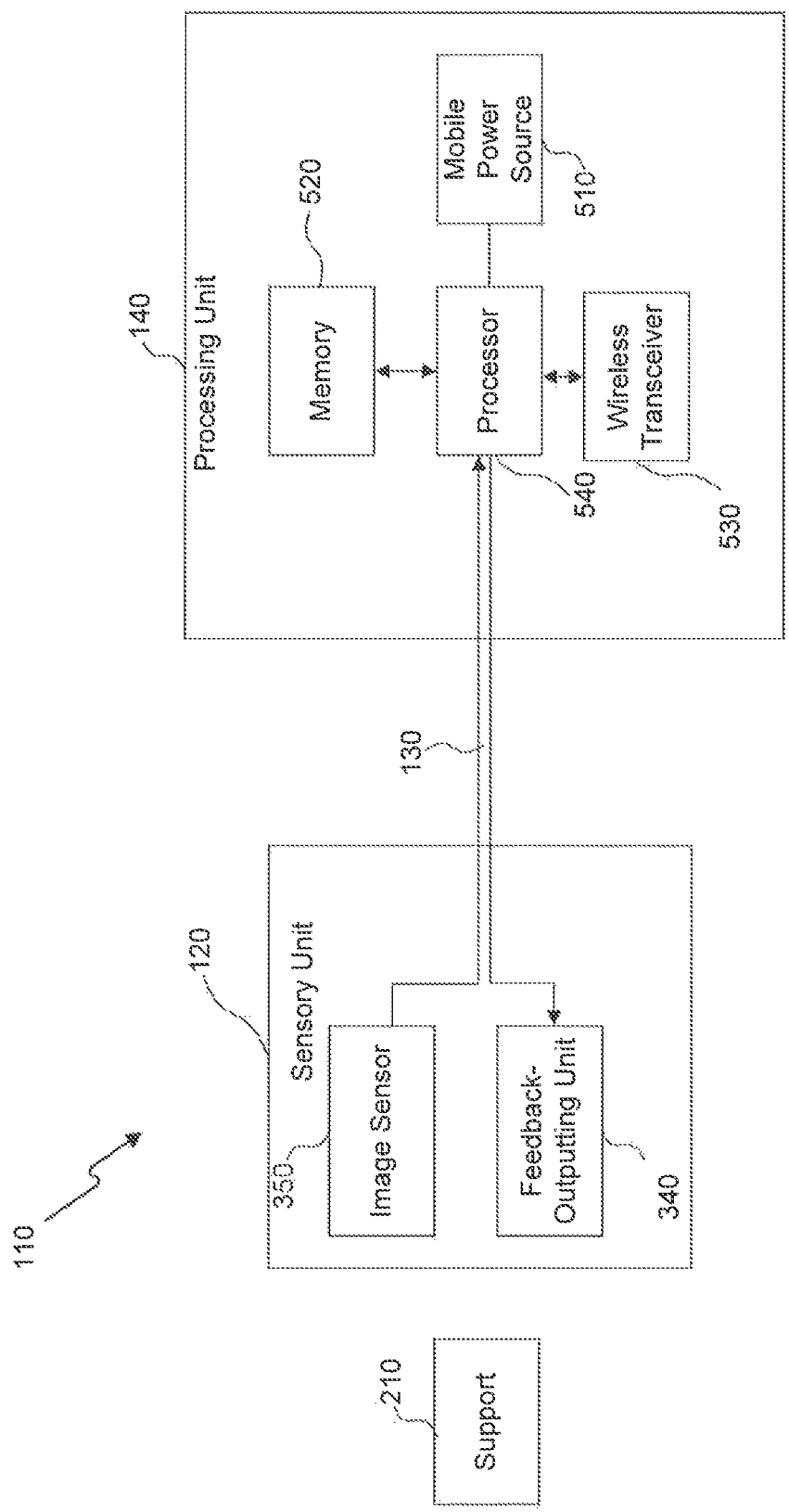
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 510 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
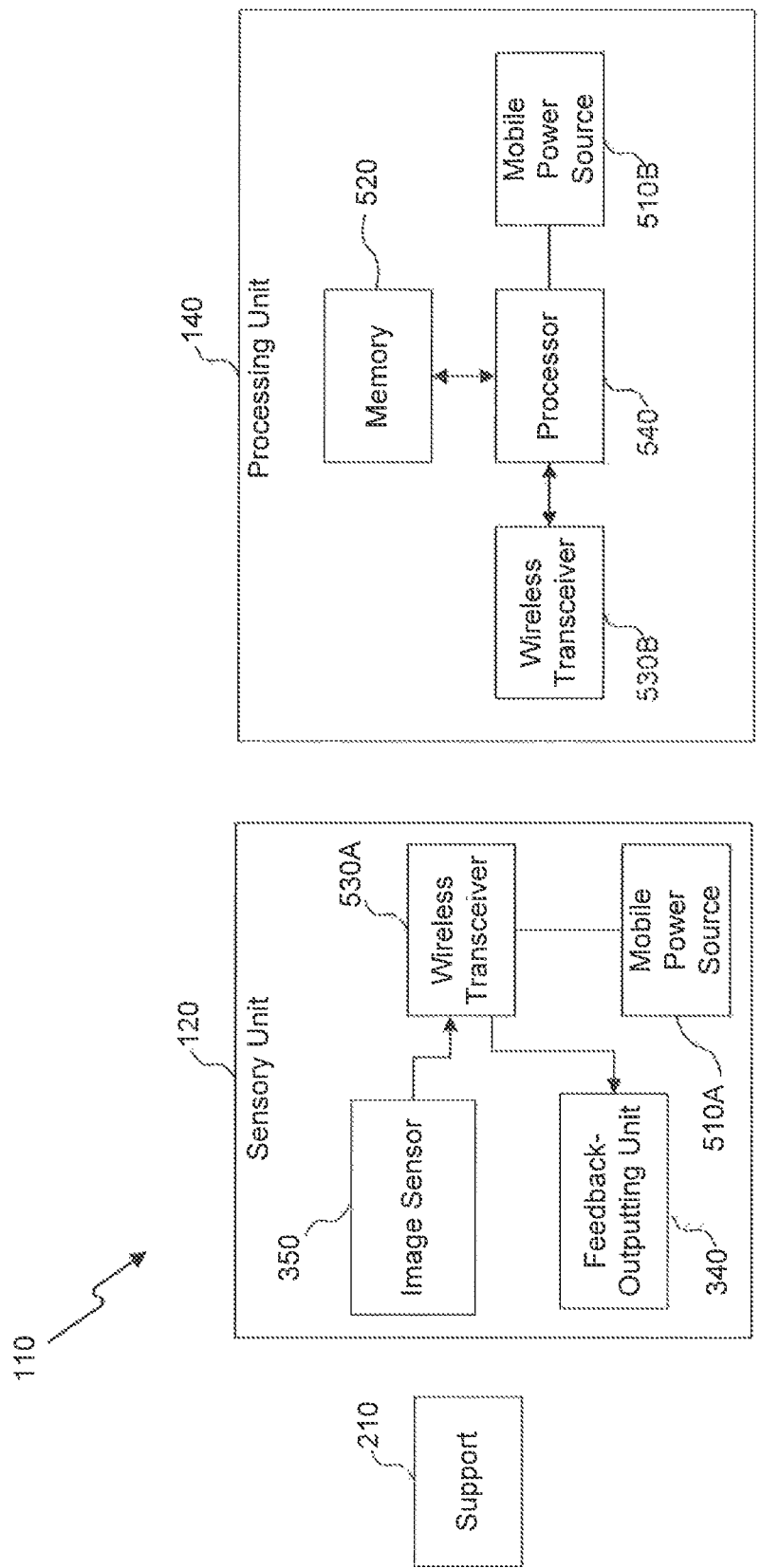
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
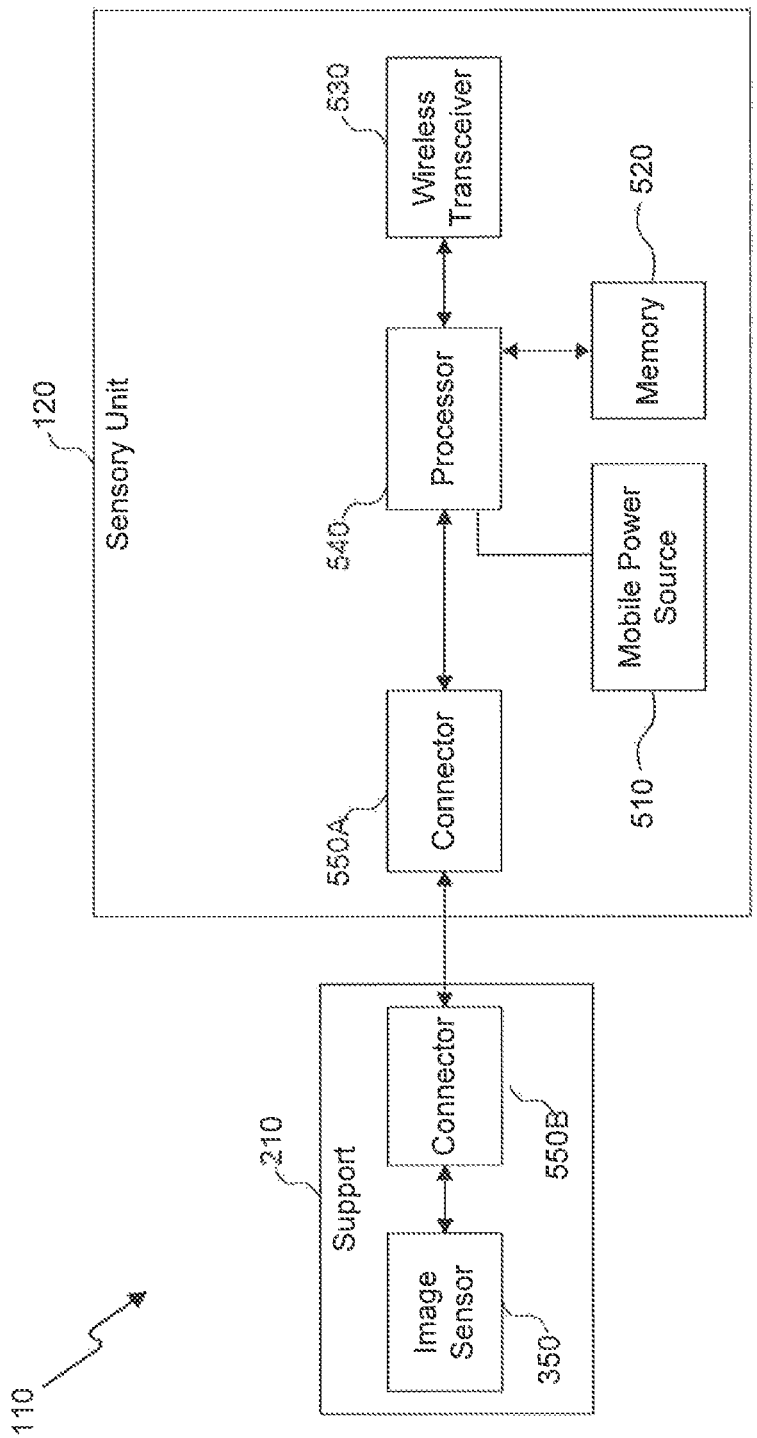
FIG. 5O is a block diagram illustrating an example of the components of an apparatus for aiding persons who have low vision according to a third embodiment.
FIG. 5D is a block diagram illustrating an example of the components of an apparatus for aiding persons who have low vision according to a fourth embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
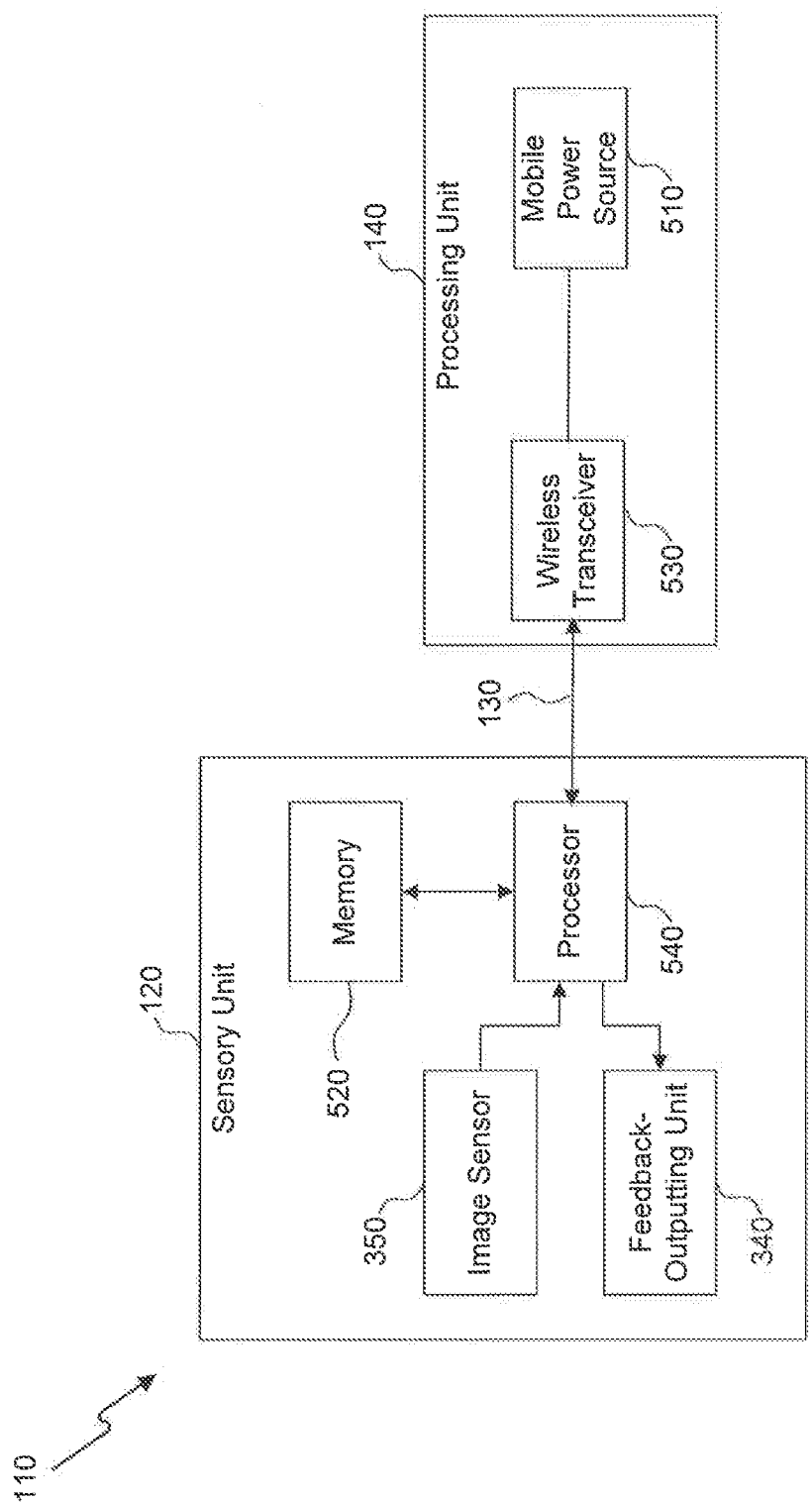

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides an object information function. The object information function may allow apparatus 110 to provide feedback to a user based on an identified object and information associated with the object. In this way, the user may receive information related to the object.

As has been described, apparatus 110 may be configured to identify objects from real-time images captured (e.g., by image sensor 350) from an environment of a user of apparatus 110. Many objects may provide information that people may use to understand their environment and make decisions. For example, a road sign (e.g. a speed-limit sign) includes information (e.g., the speed-limit of a road) observable by individuals who view the road sign. In some embodiments, apparatus 110 may be configured to identify an object and provide feedback to a user such that the user understands information provided by or associated with the object.

Further, many objects change state over time, where each state may represent different information to people who view the object. For example, a traffic light may change colors and/or signals over time (e.g., red to green, walk to don't walk, etc.), with each color and/or signal conveying different information (e.g., safe or unsafe to go/walk). In some embodiments, apparatus 110 may be configured to identify and monitor an object, and use information associated with an object to provide appropriate feedback to a user, such as feedback indicating that the object is capable of changing states, is likely to change states, has changed its state, etc. As used herein, an object has "changed its state" when any aspect of the object is different from a previous point in time. For example, an object may change its state when the object, or any part, portion, and/or component of the object, changes its appearance, moves locations, changes properties (e.g., temperature), receives another object, has a portion or component thereof removed, etc.

Figure 6:
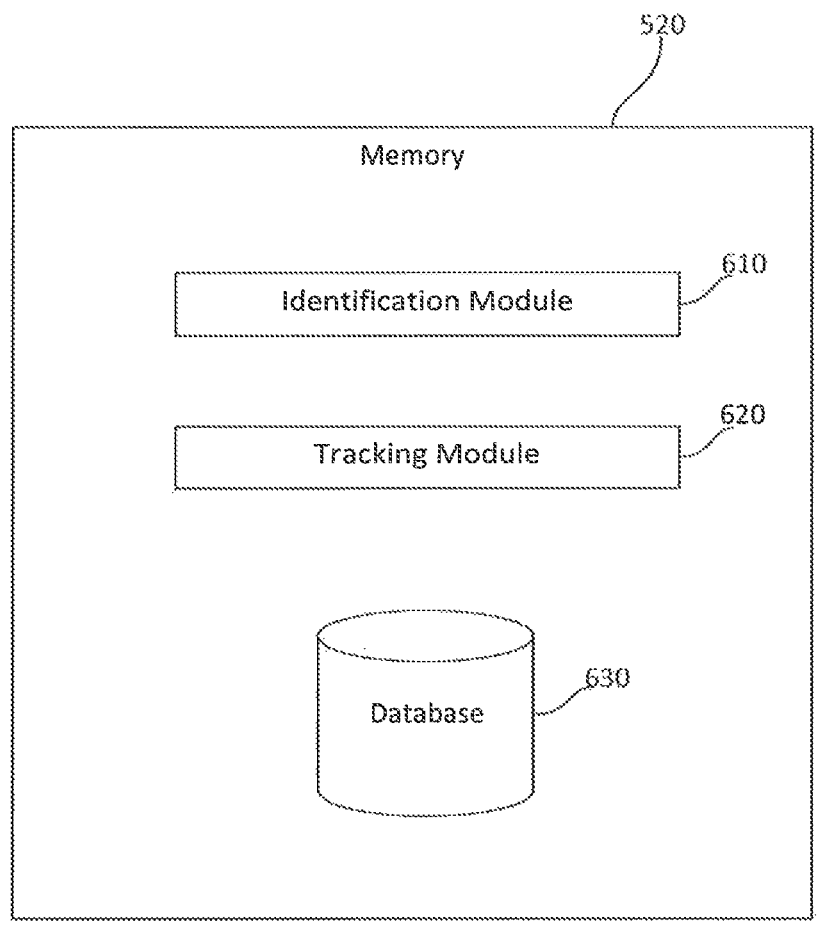
FIG. 6 is a block diagram illustrating an example of a memory configured to provide an object information function, consistent with disclosed embodiments.

In some embodiments, memory 520 may include components configured to provide the object information function. As shown in FIG. 6, memory 520 may include an identification module 610, a tracking module 620, and a database 630. Identification module 610 may be a component configured to identify an object in real-time images captured by apparatus 110. Tracking module 620 may be a component configured to track an identified object in the captured real-time images over time. Database 630 may be a component configured to store data associated with the object information function and provide particular data when requested.

Identification module 610 and tracking module 620 may be implemented in software, hardware, firmware, a mix of any of those, or the like. For example, if identification module 610 and tracking module 620 are implemented in software, they may be stored in memory 520, as shown in FIG. 6. Other components of processing unit 140 and/or sensory unit 120 may be configured to perform processes to implement and facilitate operations of identification module 610 and tracking module 620. Thus, identification module 610 and tracking module 620 may include software, hardware, or firmware instructions (or a combination thereof) executable by one or more processors (e.g., processor 540), alone or in various combinations with each other. For example, identification module 610 and tracking module 620 may be configured to interact with each other and/or other modules of apparatus 110 to perform functions consistent with disclosed embodiments.

Database 630 may include one or more memory devices that store information and are accessed and/or managed through a computing device, such as processing unit 140. In some embodiments, database 630 may be located in memory 520, as shown in FIG. 6. In other embodiments, database 630 may be located remotely from memory 520, and be accessible to other components of apparatus 110 (e.g., processing unit 140) via one or more wireless connections (e.g., a wireless network). While one database 630 is shown, it should be understood that several separate and/or interconnected databases may make up database 630. Database 630 may include computing components (e.g., database management system, database server, etc.) configured to receive and process requests for data stored in memory devices associated with database 630 and to provide data from database 630.

In some embodiments, database 630 may be configured to store data associated with the object information function of apparatus 110. For example, database 630 may include recognized objects. In some embodiments, recognized objects may include images of objects that were previously stored via apparatus 110. Recognized objects may be objects that apparatus 110 is configured to identify in real-time image data received by image sensor 350. Recognized objects may include any physical object, a person, an area, an environment, a background, and any combination and/or grouping of these. Recognized objects may include a particular aspect of an object (e.g., shape, color, text, etc.). In some embodiments, database 630 may also store information indicating whether a recognized object is associated with an object that is likely to change its state, as will be described in more detail below.

In some embodiments, recognized objects may include triggers, including triggers associated with the object information function of apparatus 110. In some embodiments, triggers may be any stored image or portion of an image that apparatus 110 may recognize as an input indicating a particular intention of the user of apparatus 110. For example, a pointing finger, a specific object, a particular hand motion, change in the field-of-view of apparatus 110, change in the user's area of focus, and the like, may be triggers. In some embodiments, apparatus 110 may be configured to perform a process to match a trigger in real-time image data to a trigger stored in database 630 and perform additional processing to determine whether an object is likely to change states, a state of an object, etc.

In some embodiments, apparatus 110 may be configured to use the object information function to provide information associated with an object to a user. In one example, apparatus 110 may identify an object, determine information associated with the object, and provide feedback to the user based on the determined information, such as audible feedback through feedback-outputting unit 340. In some embodiments, apparatus 110 may also be configured to perform additional processing to determine if an object is likely to change its state and provide feedback based on the results of the determination. In instances in which apparatus 110 determines that an object is likely to change its state, apparatus 110 may be configured to perform additional processing to track the object and provide feedback based on the state of the object, including feedback before and after an object changes states.

Identification module 610 and tracking module 620 may be implemented in software, hardware, firmware, a mix of any of those, or the like. For example, if the modules are implemented in software, they may be stored in memory 520, as shown in FIG. 6. Other components of processing unit 140 and/or sensory unit 120 may be configured to perform processes to implement and facilitate operations of the modules. Thus, identification module 610 and tracking module 620 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., identification module 610 and tracking module 620) may each include dedicated sensors (e.g., IR, image sensors, etc.) and/or dedicated application processing devices to perform the functionality associated with each module.

As used herein, real-time image data may refer to image data captured in real-time or near real-time. For example, identification module 610 may monitor the field-of-view of apparatus 110 to detect inputs while tracking module 620 may track objects. Accordingly, identification module 610 and tracking module 620 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 7:
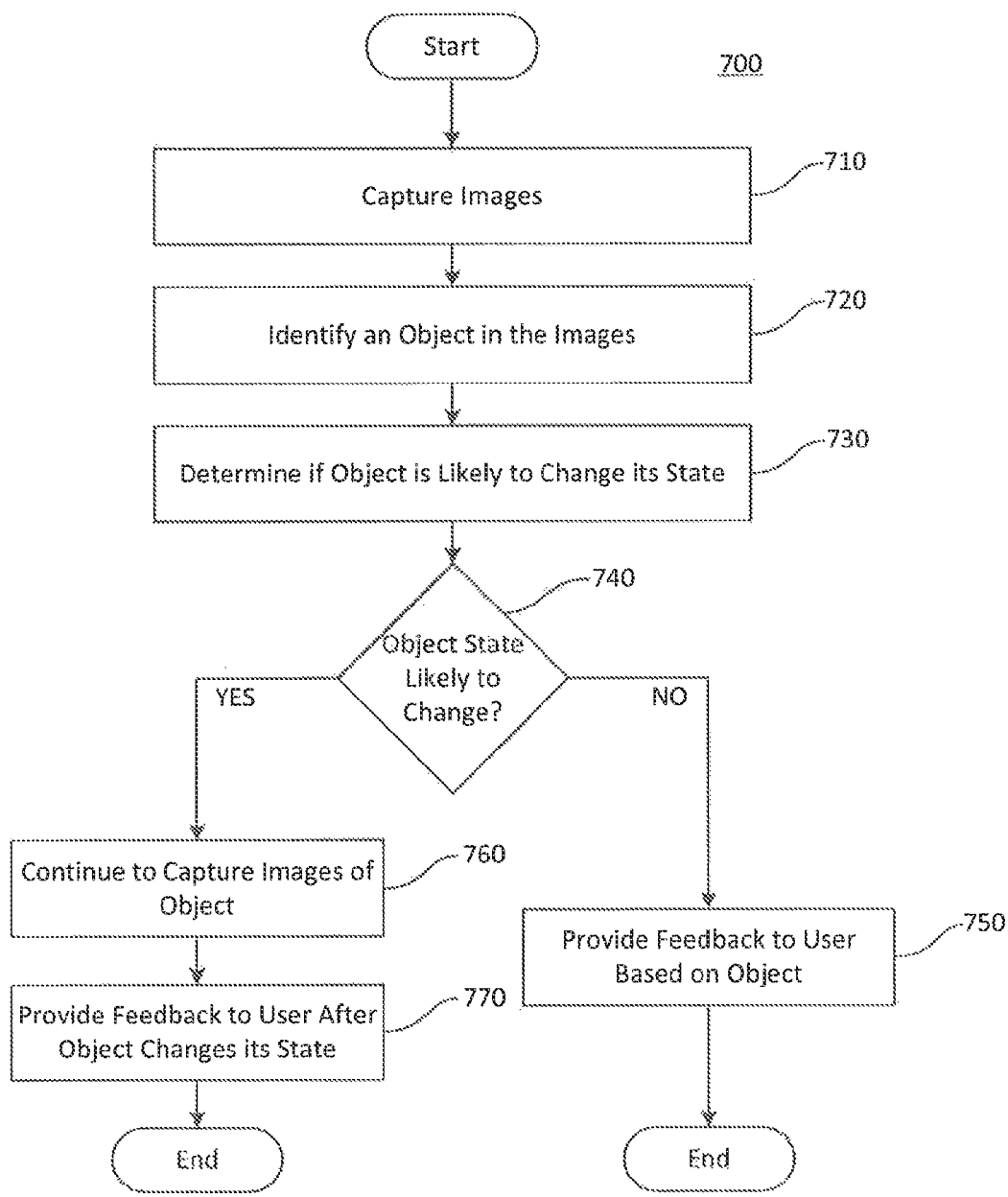
FIG. 7 is a flowchart of an example of a process for providing feedback to a user as part of an object information function, consistent with disclosed embodiments.

FIG. 7 depicts an example of a process 700 for providing feedback to a user as part of an object information function of apparatus 110. In one embodiment, apparatus 110 may be configured to perform process 700 to provide information associated with an object to a user, the information depending on a determination of whether the object is likely to change states and, if it is likely to change states, the state of the object.

As apparatus 110 operates, image sensor 350 may capture real time images from an environment of the user (step 710). Image sensor 350 may capture the images as image data. In some embodiments, identification module 610 may be configured to process the received image data. For example, identification module 610 may be configured to process image data to determine if one or more of the images contain an object, such as by matching image data associated with an object to a recognized object stored in database 630. Based on the determination, identification module 610 may identify an object in the real-time image(s) (step 720).

In some embodiments, apparatus 110 may be configured to initially process at least one image captured by image sensor 350 to determine whether an object in the environment of the user is likely to change its state. For example, identification module 610 may be configured to process received image data to determine whether an identified object is an object that is likely to change its state (step 730). As used herein an object is "likely to change its state" when the object is capable of changing its state and information associated with the object indicates that the change in state may occur while the object remains in the environment of the user. Examples of changes in state of an object may include a change in color, position, operation, or display of information associated with an object.

The information associated with the object indicating that the object is likely to change states may include any type or form of information. In one example, the information may include stored information associated with the object. For example, the information may include a type of the object identified in the image(s). The type of the object may be stored as information associated with recognized objects in database 630. Types of objects may include, for example, readily-movable objects (e.g., people, vehicles, hand-held objects, etc.), signals (e.g., stop lights), and displays (e.g., electronic signs, computer screens, televisions, etc.). In some embodiments, an object may only be "likely to change its state" when the object matches a recognized object stored in database 630 that is associated with information that indicates that the object is a type of object that is likely to change its state. For example, a pedestrian gate in a subway, which may be at an open or closed position.

In another example, the information associated with the object indicating that the object is likely to change states may include additional information that is determined from the image data. Identification module 610 may be configured to, in addition to identifying objects, identify additional information from at least one of the captured images, which may include additional objects, contextual information, etc. For example, identification module 610 may be configured to identify a portion of a user's hand in the captured image(s). The portion of the user's hand may be placed in relation to an identified object in such a way that identification module 610 may make a determination that the user is holding the identified object. For example, identification module 610 may process an image that includes a portion or portions of a user's hand (e.g., fingers) around the sides of an object. The identification of at least a portion of the user's hand may indicate that the user is holding the object and therefore the object may be readily movable. Movement of the object may constitute a change in state. In this way, identification module 610 may determine that an object is likely to change its state. In some embodiments, the portion of a user's hand holding the object may act as a trigger that indicates an object is likely to change its state. Identification module 610 may be configured to identify other triggers that indicate that an object is likely to change states in the image data. For example, identification module 610 may identify triggers such as a user pointing at an object, a head movement of a user, erratic movement of an object, among others. Similarly, identification module 610 may be configured to identify a background of an object, and use a particular context of the background of the object as information that indicates that an object is likely to change states.

It should be understood that identification module 610 may also be configured to determine if an object is unlikely to change its state. An object may be "unlikely to change its state" when the object is incapable of changing its state and/or information associated with the object indicates that the object will not change its state. In some embodiments, identification module 610 may use the same information to determine if an object is unlikely to change its state as was described with respect to determining that the object is likely to change its state. For example, identification module 610 may be configured to determine that an object is unlikely to change its state based on a type of an object identified in the image data, an identification of at least a portion of a user's hand, identification of a trigger, a particular context of a background of an object, etc. In some embodiments, identification module 610 may determine that an object is unlikely change its state in any instance in which a determination that an object is likely to change its state is not made. For example, if no information indicates that the object may change its state while the object remains in the environment of the user, then identification module 610 may assume that the object is unlikely to change its state. Similarly, identification module 610 may determine if information associated with an object indicates that the object is unlikely to change its state, and if no information provides such an indication, assume that the object is likely to change its state.

Regardless of the manner in which apparatus 110 determines whether an object is likely (and/or unlikely) to change its state, apparatus 110 may be configured to provide feedback to the user based on the object (e.g., as part of the object information function). In instances in which identification module 610 determines that the object is unlikely to change its state (step 740—NO), apparatus 110 (via identification module 610 or some other component), may be configured to provide feedback to the user. For example, if, during initial processing, a determination is made that the object is unlikely to change its state, apparatus 110 may be configured to additionally process the image data (e.g., at least one image in which the object was identified) and provide feedback to the user based on the information in the image data (step 750). For example, apparatus 110 may be configured to provide feedback (e.g., audible feedback), such as an identification of the object. In another example, apparatus 110 may determine that a traffic light isn't operational since neither of the "walk" or "don't walk" lights are on for a period of time, after which apparatus 110 may notify the user.

In instances in which identification module 610 determines that an object is likely to change its state (step 740—yes), apparatus 110 may be configured to perform additional processing to provide appropriate feedback to the user. For example, if, during initial processing, a determination is made that the object is likely to change its state, apparatus 110 may be configured to capture images of the object (step 760) and alert the user with feedback after a change in state of the object occurs (step 770). For example, tracking module 620 may be configured to track an object throughout one or more additional images of the object, and identification module 610 may be configured to continue to process image data associated with the tracked object and determine that the object has changed its state. After this type of identification is made, apparatus 110 may be configured to provide feedback (e.g., audible feedback) to the user, such as an indication that the state of the object has changed and/or an indication of the state of the object. In some embodiments, apparatus 110 may also be configured to provide feedback (e.g., audible feedback) to the user based on the initial state of the object (e.g., before the object changes states), such as an indication that an identified object is likely to change states and/or an indication of the state of the object at that time.

Apparatus 110 may perform process 700 to provide a user with information about an object, including an object that is likely to change its state. The information may include an initial state of an object and a subsequent state of an object (e.g., after a change in state). Apparatus 110 may provide information associated with each state of an object to a user, such that the user may understand what information the object is conveying at the time, and make appropriate decisions based on the information. In this way, a visually-impaired user of apparatus 110 may be able to interact with objects in their environment, even though they may be unable to visually identify information associated with an object.

Figure 8:
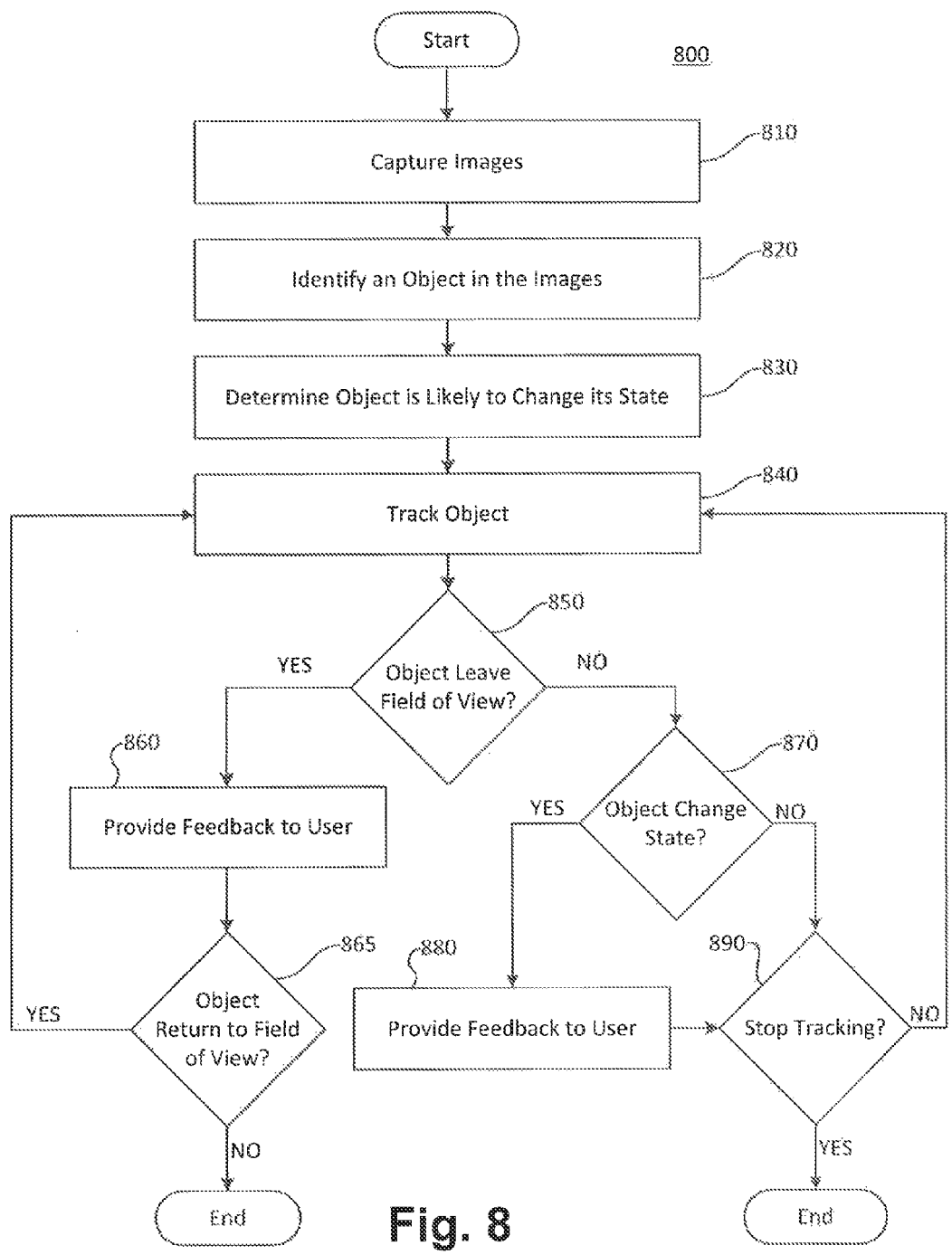
FIG. 8 is a flowchart of another example of a process for providing feedback to a user as part of an object information function.

FIG. 8 depicts another example of a process 800 for providing feedback to a user as part of the object information function of apparatus 110. In one aspect, process 800 may be performed by apparatus 110 in instances in which an identified object is determined to be likely to change its state. In some embodiments, identification module 610 and tracking module 620 may be configured to perform process 800 to provide a user with feedback about an object that is likely to change its state. To perform process 800, apparatus 110 may be arranged with image sensor 350 configured to capture real-time images from an environment of a user (step 810). In some embodiments, image sensor 350 may also be configured to be worn by a user such that a field-of-view of image sensor 350 (e.g., the detectable area) substantially coincides with a field-of-view of the user (e.g., the area a visually-unimpaired user may be configured to see).

As has been described in relation to other disclosed processes, apparatus 110 may be configured to process real-time images to determine an existence of an object in the field-of-view of image sensor 350 (step 820). For example, identification module 610 may process received image data to match a portion of an image to a recognized object stored in database 630.

Apparatus 110 may be further configured to determine whether a state of the object is likely to change. Identification module 610 may determine whether a state of the object is likely to change in a manner that is the same or similar to the determination process described in step 740 of process 700. In the example of process 800, identification module 610 may determine that an identified object is likely to change its state (step 830).

In some embodiments, apparatus 110 may be configured to track the identified object (step 840). In some aspects, apparatus 110 may track the object, while the object remains within the field-of-view of the image sensor, to determine when the change of state occurs. For example, after an object has been identified in an image, tracking module 620 may be configured to monitor subsequent images for existence of the object and any change in state of the object.

During tracking of an object, tracking module 620 may determine if the object leaves the field-of-view of image sensor 350 (step 850). An object may leave the field-of-view of image sensor 350, for example, when the user moves his or her head in such a way that image sensor 350 is directed away from the object, when the object moves to a location outside the field-of-view of image sensor 350, when another object blocks the tracked object from being captured in an image, etc.

In instances in which tracking module 620 determines that the object has left the field-of-view of image sensor 350 (step 850—YES), apparatus 110 (e.g., through tracking module 620) may be provide feedback to the user of apparatus 110 (step 860). For example, apparatus 110 may provide an indication, such as an audible indication, when the object exits the field-of-view of image sensor 350. The feedback may serve as an indication that an object that was being tracked is no longer in the images being captured by apparatus 110, and, therefore, apparatus 110 may not be able to provide additional feedback if the object changes states.

Tracking module 620 (and/or identification module 610) may be configured to determine if the object returns to the field-of-view of image sensor 350 (step 865). If and when the object returns to the field-of-view of image sensor 350 (e.g., it reappears in the image data) (step 865—YES), tracking module 620 may automatically resume following (e.g., tracking) the object (e.g., at step 840). In some embodiments, tracking module 620 may be configured to resume following the object if the object reappears in the field-of-view of image sensor 350 with a predetermined period of time. If the object does not return to the field-of-view of image sensor (step 865—NO), in a predetermined period of time, for example, apparatus 110 may stop performing processes associated with the object and process 800 may end.

While tracking module 620 continues to track an object that remains in the field-of-view of image sensor 350 (step 850—NO), identification module 610 (and/or tracking module 620) may be configured to determine if the object has changed its state (step 870). For example, identification module 610 may monitor image data to determine if an object in an image (e.g., a tracked object) is in a state that is different from previous images of the object.

In some embodiments, in instances when apparatus 110 determines that a state of an object has changed (step 870—YES), apparatus 110 (e.g., through identification module 610) may provide feedback to the user (step 880). For example, apparatus 110 may be configured to provide audible feedback to the user. The audible feedback may include information such as an indication that the object changed states, an indication of the state to which the object changed, information that is intended to be conveyed by the state of the object, etc. In some embodiments, apparatus 110 may be configured to provide a plurality of audible feedbacks, each audible feedback being associated with a specific change in the state of an object.

Tracking module 620 may be further configured to determine whether to stop tracking an object (step 890). In instances in which a determination that a tracked object has changed states has not yet been made (step 870—NO), tracking module 620 may be configured to determine whether the object should continue to be tracked. Even in instances in which an object did change its state and feedback was provided to the user, tracking module 620 may determine whether the object should continue to be tracked, such as to identify subsequent changes in a state of the object.

If tracking module 620 determines that the object should continue to be tracked (step 890—NO), process 800 may return to step 840, where tracking module 620 may continue to monitor real-time images to follow the object. In this way, if the object changes states (for the first time and/or a subsequent time), apparatus 110 may provide feedback to the user. Process 800 may continue through iterations of tracking an object and providing feedback each time it leaves a field-of-view and/or changes states, as long as tracking module 620 determines that the object should continue to be tracked. However, if tracking module 620 determines that tracking of the object should stop (step 890—YES), apparatus 110 may stop performing processes associated with the object and process 800 may end. For example, apparatus 110 may be configured to stop tracking an object after a predetermined number of changes in the state of the object has occurred, after a predetermined period of time, after a predetermined period of time without any change to the state of an object, etc.

Through example processes 700 and 800, apparatus 110 may identify an object and alert a user to the state of the object. For example, apparatus 110 may be configured to identify an object as a traffic light. A traffic light may include multiple lights, each which illuminate in a different color (e.g., red, yellow, green) to indicate different information to a viewer of the traffic light (e.g., stop, slow, go). As applied to the disclosed embodiments, a change of a state of the traffic light may include a change in color of the traffic light (e.g., red to green, green to yellow, yellow to red, etc.). Apparatus 110 may be configured to perform processes 700 and/or 800 to identify the traffic light, track the traffic light, and alert a user when the traffic light changes states (e.g., turns to red, turns to green, etc.).

Figure 9B:
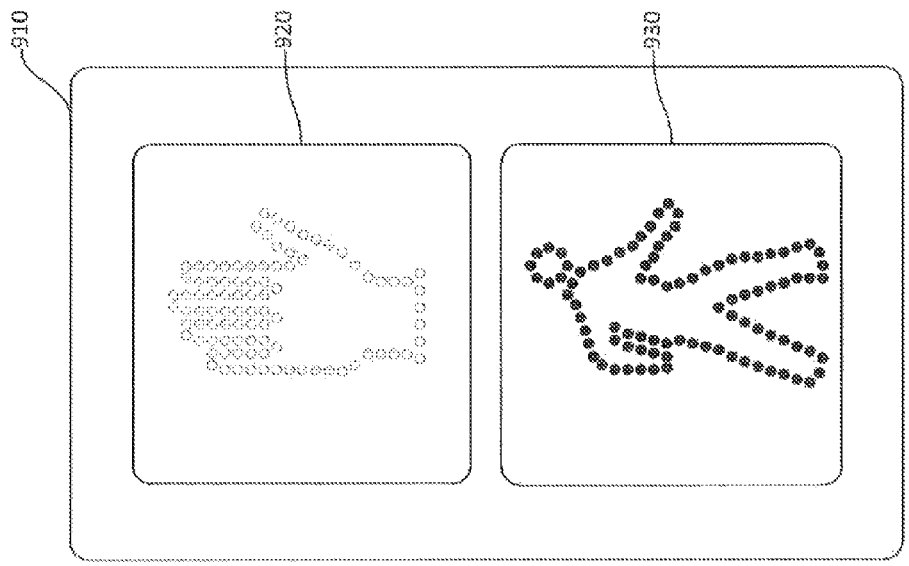
FIGS. 9A and 9B illustrate an example of a pedestrian stoplight that changes state.
Figure 9A:
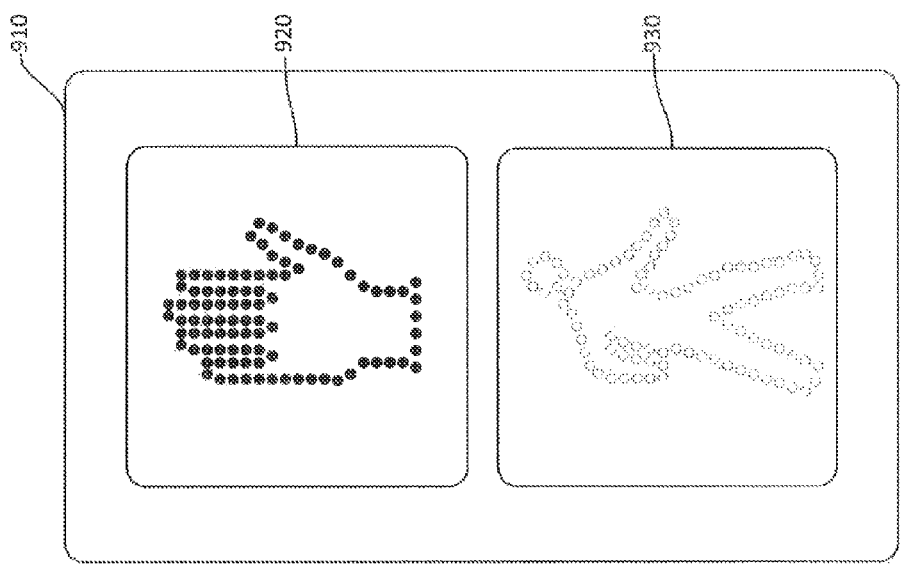

FIGS. 9A and 9B depict an example of an object that changes its state, and that may be identified by apparatus 110. As shown in FIGS. 9A and 9B, the object is a pedestrian stoplight 910 that includes a first electronic signal 920 and a second electronic signal 930. First electronic signal 920 may be a stop signal configured to be illuminated to indicate to individuals not to enter a particular crosswalk, for example. Second electronic signal 930 may be a walk signal configured to be illuminated to indicate to individuals that it may be safe to enter the crosswalk, for example.

FIG. 9A depicts an example of a first state of pedestrian stoplight 910. In the first state, first electronic signal 920 may be illuminated (e.g., with red light) and second electronic signal 930 may be dark (e.g., not illuminated). FIG. 9B depicts an example of a second state of pedestrian stoplight 910. In the second state, first electronic signal 920 may be dark (e.g., not illuminated) and second electronic signal 930 may be illuminated (e.g., with green light).

In providing an object information function, apparatus 110 may identify pedestrian stoplight 910 in at least one image captured by image sensor 350, when pedestrian stoplight 910 is in the field-of-view of image sensor 350. In addition, apparatus 110 may be configured to determine that pedestrian stoplight 910 is an object that is likely to change its state (e.g., based on the type of the object, a background of the object, a trigger, etc.). Apparatus 110 may be further configured to provide feedback to the user (e.g., an audible indicator), such as an indication of the first state of pedestrian stoplight 910 and/or associated information (e.g., "the stoplight is red," "do not walk," etc.).

Apparatus 110 may also be configured to track pedestrian stoplight 910, while it remains in the field-of-view of image sensor 350. If the pedestrian stoplight 910 leaves the field-of-view of image sensor 350, apparatus 110 may provide feedback to the user to indicate that the user should return stoplight 910 to the field-of-view (e.g., "lost view of the stoplight," "please look at the stoplight," etc.). When the pedestrian stoplight 910 changes from the first state (FIG. 9A) to the second state (FIG. 9B), apparatus 110 may provide feedback to the user, such as an indication of the second state of stoplight 910 and/or associated information (e.g., "the stoplight is green," "safe to cross," etc.).

Figure 10A:
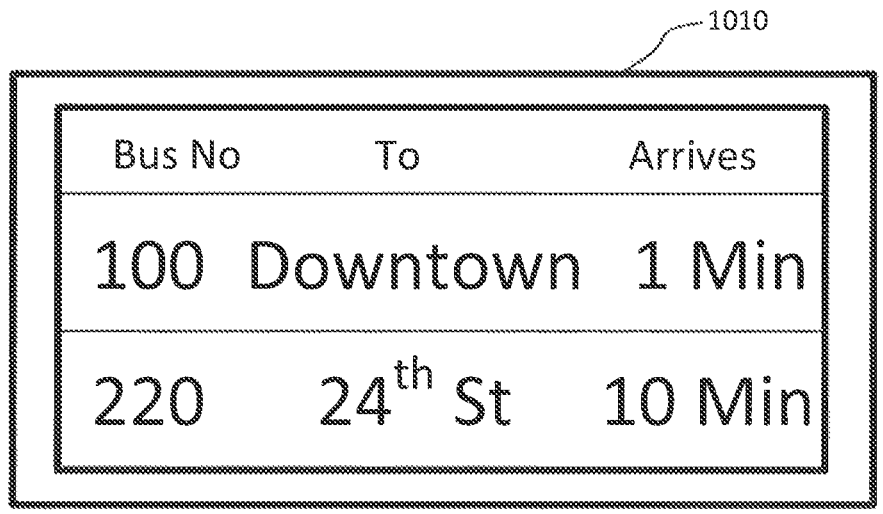
FIGS. 10A and 10B illustrate an example of an electronic display that changes state.
Figure 10B:
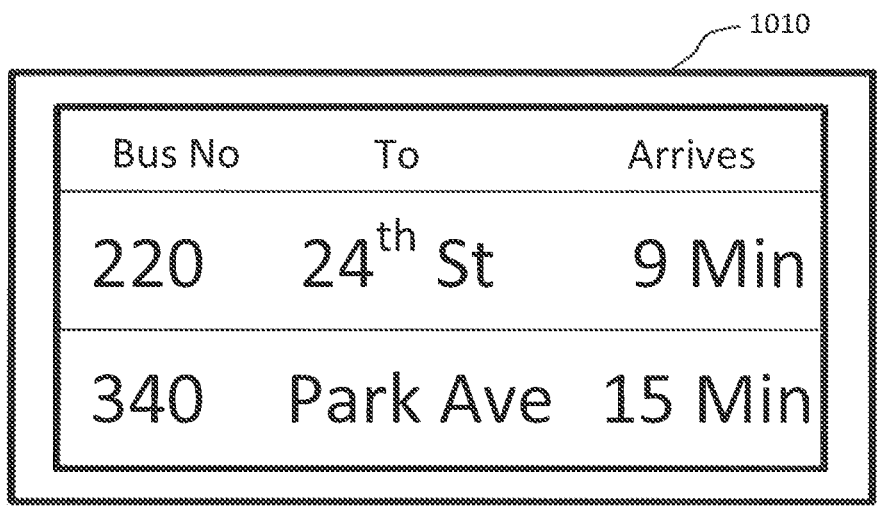

It should be understood that the disclosed embodiments may be used to apply the object information function to many different objects that may change states in a variety of ways. For example, apparatus 110 may use similar processing to identify an electronic display and provide feedback to a user to identify a change in state of the electronic display, including an update to the text of an electronic display. In this way, a user may be alerted to a change in information on a sign. FIGS. 10A and 10B illustrate an example of an electronic display 1010 that includes textual information identifying the arrival time of a public transportation vehicle. FIG. 10A may depict a first state of electronic display 1010 and FIG. 10B may depict a second state of electronic display 1010. Apparatus 110 may be configured to provide feedback associated with the first state of electronic display 1010 (e.g., audibly read the text). Consistent with disclosed embodiments, apparatus 110 may also be configured to determine that electronic display 1010 is likely to change its state and track electronic display 1010 in captured image data. After electronic display changes from the first state to the second state, apparatus 110 may determine that state has changed, and provide additional feedback to the user, such as an indication that electronic sign 1010 has changed states and/or information associated with the second state (e.g., audibly read the text).

In another example, apparatus 110 may be configured to identify a person as an object and provide feedback to the user based on a change in state of the person. For example, apparatus 110 may be configured to monitor a facial expression of the person and provide feedback when a facial expression of the person changes (e.g., the person smiles, frowns, etc.). In this way, the user may be alerted to a visual characteristic of a person that may communicate particular information about the person (e.g., the person is happy, sad, angry, etc.). For example, a visually-impaired user may want to know if a person (e.g., a store clerk) in front of them is looking at them (and is awaiting a reply, for example).

In another example of the object information function, apparatus 110 may be configured to identify readily-movable objects and provide feedback based on the movement of the object. For example, apparatus 110 may be configured to identify a vehicle (including stationary vehicles and moving vehicles), which may also be determined to be an object that is likely to change its state.

For example, apparatus 110 may identify a public transportation vehicle in the image data. Apparatus 110 may be configured to identify an appearance of the public transportation vehicle in the environment of the user as a change in state of the object. In this way, apparatus 110 may be configured to provide feedback to a user to indicate that a public transportation vehicle has arrived (e.g., and/or is ready to be boarded). Similarly, apparatus 110 may be configured to identify a change in direction or speed of a moving vehicle as a change in state of an object. In this way, the user may be alerted to the movement of vehicles in their environment.

Another example of a change in state of a readily-movable object may include the appearance of a portion of the object in the image data. For example, an object may include text on at least a portion of the object. Apparatus 110 may identify an appearance of the text on the object in the environment of the user as a change in state of the object and provide feedback to the user based on this change (e.g., audibly read the text to the user). In some instances, apparatus 110 may identify an object that includes text at least a part of which is not viewable by the image sensor, where the change in state of the object may include an appearance of at least a part of the text to image sensor 350. Further, it should be understood that movement of the user to bring an object, or a portion of an object, into the field-of-view of image sensor 350 may constitute a similar change in state of an object, causing apparatus 110 to provide appropriate feedback.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for processing images, the apparatus comprising:
    an image sensor configured to be worn by a visually impaired user and configured to capture real time images from an environment of the user; and
    at least one processor device configured to:
        initially process at least one image of the captured real time images to identify an object in the environment of the user that is likely to change its state;
        provide a first feedback to the user that indicates a current state of the object;
        after providing the first feedback, determine that the object has left a field of view of the image sensor;
        after determining that the object has left the field of view of the image sensor, provide a second feedback to the user that indicates the object is no longer in the field of view of the image sensor;
        after providing the second feedback, determine that the object has reappeared in the field of view of the image sensor; and
        after determining that the object has reappeared in the field of view of the image sensor, continue to capture images of the object and alert the user with a third feedback after a change in the state of the object occurs, wherein the third feedback indicates a new state of the object,
    wherein the change of state includes at least one of a change in color, a change in position, and a change in display of information, and the change of state is determined while the object remains in the field of view of the image sensor.

2. The apparatus of claim 1, wherein the first feedback, the second feedback, and the third feedback are audible.

3. The apparatus of claim 1, wherein the object includes a traffic light and the change of state includes a change in color of the traffic light.

4. The apparatus of claim 3, wherein the at least one processor device is further configured to provide the first feedback when the traffic light is green or red, and alert the user with the third feedback after the traffic light turns from green to red or after the traffic light turns from red to green.

5. The apparatus of claim 1, wherein the object includes text on an electronic display and the change of state includes an update to the text on the electronic display.

6. The apparatus of claim 1, wherein the object includes a person, and the change of state includes a change in a facial expression of the person.

7. The apparatus of claim 1, wherein the object includes a moving vehicle and the change of state includes a change in direction or speed of the moving vehicle.

8. The apparatus of claim 1, wherein the at least one processor device is further configured to that a second object is unlikely to change its state based on at least one of: a type of the object in the at least one image, an identification of at least a portion of a user's hand, identification of a trigger, and a particular context of a background of the object.

9. The apparatus of claim 1, wherein the determination that the object is likely to change its state is based on at least one of: a type of the object in the image, an identification of at least a portion of a user's hand, identification of a trigger, and a particular context of a background of the object.

10. The apparatus of claim 1, wherein the image sensor is further configured to be movable with a head of the user such that a field of view of the image sensor substantially coincides with a field of view of the user.

11. The apparatus of claim 10, wherein upon determining that the object is likely to change its state, the at least one processor device is further configured to track the object, while the object remains within the field of view of the image sensor, to determine when the change of state occurs.

12. The apparatus of claim 11, wherein after the object exits the field of view of the image sensor, the at least one processor device is further configured to automatically resume following the object when the object reappears in the field of view of the image sensor.

13. The apparatus of claim 11, wherein after the object exits the field of view of the image sensor, the at least one processor device is further configured to resume following the object if the object reappears in the field of view of the image sensor within a predetermined period of time.

14. An apparatus for processing images, the apparatus comprising:
    an image sensor configured to be worn by a visually impaired user such that a field of view of the image sensor substantially coincides with a field of view of the user, and to capture real time images from an environment of the user; and
    at least one processor device configured to:
        process the captured real time images to determine an existence of an object in the field of view of the image sensor;
        determine that a state of the object is likely to change;
        provide a first feedback to the user that indicates a current state of the object;
        after providing the first feedback, determine that the object has left the field of view of the image sensor;
        after determining that the object has left the field of view of the image sensor, provide a second feedback to the user that indicates the object is no longer in the field of view of the image sensor;

after providing the second feedback, determine that the object has reappeared in the field of view of the image sensor; and after determining that the object has reappeared in the field of view of the image sensor, track the object while the object remains within the field of view of the image sensor and provide a third feedback to the user after the state of the object has changed, wherein the third feedback indicates a new state of the object, wherein the change of state includes at least one of a change in color, a change in position, and a change in display of information, and the change of state is determined while the object remains in the field of view of the image sensor.

15. The apparatus of claim 14, wherein the at least one processor device is further configured to provide a plurality of audible feedbacks, each audible feedback being associated with a specific change in the state of the object.

16. The apparatus of claim 14, wherein the at least one processor device is further configured to stop tracking the object after a predetermined number of changes in the state of the object have occurred.

17. The apparatus of claim 14, wherein the at least one processor device is further configured to stop tracking the object after a predetermined period of time.

18. The apparatus of claim 14, wherein the at least one processor device is further configured to stop tracking the object after a predetermined period of time without any change to the state of the object.

19. A method for providing feedback to a visually impaired user, the method comprising:

receiving from an image sensor real time image data from an environment of the user, wherein the image sensor is configured to be positioned for movement with a head of the user;

processing the image data to determine that a state of an object in the environment of the user is likely to change;

providing a first audible feedback to the user indicating a current state of the object;

after providing the first audible feedback, determining that the object has left a field of view of the image sensor;

after determining that the object has left the field of view of the image sensor, providing a second audible feedback to the user that indicates the object is no longer in the field of view of the image sensor;

after providing the second audible feedback, determining that the object has reappeared in the field of view of the image sensor; and after determining that the object has reappeared in the field of view of the image sensor, tracking the object while the object remains within the field of view of the image sensor and providing a third audible feedback to the user after the state of the object has changed, wherein the third audible feedback indicates a new state of the object, wherein the change of state includes at least one of a change in color, a change in position, and a change in display of information, and the change of state is determined while the object remains in the field of view of the image sensor.

20. A software product stored on a non-transitory computer readable medium and comprising data and computer implementable instructions for carrying out the method of claim 19.

* * * * *

UNITED STATES PATENT AND TRADEMARK OFFICE
CERTIFICATE OF CORRECTION

PATENT NO. : 9,189,973 B2
APPLICATION NO. : 14/135775
DATED : November 17, 2015
INVENTOR(S) : Yonatan Wexler et al.

Page 1 of 1

It is certified that error appears in the above-identified patent and that said Letters Patent is hereby corrected as shown below:

IN THE CLAIMS

In claim 8, column 24, line 19, "to that" should read as --to determine that--.

Signed and Sealed this
Fifth Day of April, 2016

Michelle K. Lee
*Director of the United States Patent and Trademark Office*